(12) United States Patent
Radocea et al.

(10) Patent No.: US 12,318,370 B2
(45) Date of Patent: Jun. 3, 2025

(54) PROCESSES FOR PREPARING SOLID STATE FORMS

(71) Applicant: Varda Space Industries, Inc., El Segundo, CA (US)

(72) Inventors: Adrian Radocea, Long Beach, CA (US); Jordan Michael Croom, Los Angeles, CA (US); Larry Robin Chan, Torrance, CA (US); Ami Sanat Bhavsar, Hermosa Beach, CA (US); Pamela A. Smith, West Lafayette, IN (US); Stephen R. Byrn, West Lafayette, IN (US); Stephan D. Parent, West Lafayette, IN (US); Dale K. Purcell, West Lafayette, IN (US)

(73) Assignee: Varda Space Industries, Inc., El Segundo, CA (US)

( * ) Notice: Subject to any disclaimer, the term of this patent is extended or adjusted under 35 U.S.C. 154(b) by 0 days.

(21) Appl. No.: 18/622,657

(22) Filed: Mar. 29, 2024

(65) Prior Publication Data

US 2024/0269118 A1    Aug. 15, 2024

Related U.S. Application Data

(63) Continuation of application No. PCT/US2023/031719, filed on Aug. 31, 2023.

(60) Provisional application No. 63/510,042, filed on Jun. 23, 2023, provisional application No. 63/404,090, filed on Sep. 6, 2022, provisional application No. 63/403,258, filed on Sep. 1, 2022.

(51) Int. Cl.
  *A61K 31/427*    (2006.01)
  *A61K 31/4025*   (2006.01)
  *C07D 277/28*    (2006.01)

(52) U.S. Cl.
  CPC ........ *A61K 31/427* (2013.01); *A61K 31/4025* (2013.01); *C07D 277/28* (2013.01)

(58) Field of Classification Search
  CPC ............................ A61K 31/427; C07D 277/28
  See application file for complete search history.

(56) References Cited

U.S. PATENT DOCUMENTS 7,148,359 B2    12/2006    Chemburkar et al.

FOREIGN PATENT DOCUMENTS

WO    WO 2008/041176 A2    4/2008

OTHER PUBLICATIONS

Chemburkar, S.R., et al., "Dealing with the Impact of Ritonavir Polymorphs on the Late Stages of Bulk Drug Process Development," Organic Process Research & Development, 2000, vol. 4, Issue 5, pp. 413-417, XP093117689.
International Search Report and Written Opinion, Patent Cooperation Treaty Application No. PCT/US2023/031719, dated Mar. 19, 2024, 23 pages.
Kawakami, K., et al.; "Relationship between Crystallization Tendencies during Cooling from Melt and Isothermal Storage: Toward a General Understanding of Physical Stability of Pharmaceutical Glasses," Molecular Pharmaceutics, 2014, 11, pp. 1835-1843, XP093116658.
Li, S., et al. "Ritonavir Revisited: Melt Crystallization Can Easily Find the Late-Appearing Polymorph II and Unexpectedly Discover a New Polymorph III," Molecular Pharmaceutics, Jul. 14, 2023, 20, pp. 3854-3863, XP093116642, https://doi.org/10.1021/acs.molpharmaceut.2c00994.
Parent, S.D., et al., "Ritonavir Form III: A Coincidental Concurrent Discovery", Crys. Growth Des.,vol. 23, No. 1, Dec. 21, 2022 (Dec. 21, 2022), pp. 320-325, XP093116629, ISSN: 1528-7483, DOI:10.1021/acs.cgd.2c01017, Retrieved from the Internet: URL:https://pubs.acs.org/doi/pdf/10.1021/acs.cgd.2c01017>.
Parent, S.D., et al., "Ritonavir Form III: Lightning strikes twice at the same time, 137 miles apart", ChemRxiv, Sep. 8, 2022 (Sep. 8, 2022), pp. 1-18, XP093116650, DOI:10.26434/chemrxiv-2022-49tzw.
Partial International Search Report and Provisional Opinion, Patent Cooperation Treaty Application No. PCT/US2023/031719, dated Jan. 24, 2024, 20 pages.
Snell, E.H., et al. "Microgravity as an environment for macromolecular crystallization—an outlook in the era of space stations and commercial space flight", Crystallography Reviews, vol. 27, No. 1, Apr. 8, 2021 (Apr. 8, 2021), pp. 3-46, XP093117846, ISSN:0889-311X, DOI:10.1080/0889311X.2021.1900833.
Yao, X., et al., "Ritonavir Form III: A New Polymorph After 24 Years", ChemRxiv, Aug. 18, 2022 (Aug. 18, 2022), pp. 1-17, XP093117430, DOI:10.26434/chemrxiv-2022-35fwp.

*Primary Examiner* — Kamal A Saeed
(74) *Attorney, Agent, or Firm* — Fenwick & West LLP

(57) ABSTRACT

The present disclosure is related to a polymorphic form of ritonavir prepared by novel methods that require less time to produce the polymorphic form, the methods of preparing the polymorphic form, pharmaceutical compositions comprising the polymorphic form produced by the provided methods, and corresponding methods of treatment with the polymorphic form produced by the provided methods.

20 Claims, 30 Drawing Sheets

PROCESSES FOR PREPARING SOLID STATE FORMS

1. BACKGROUND

Figure 1:
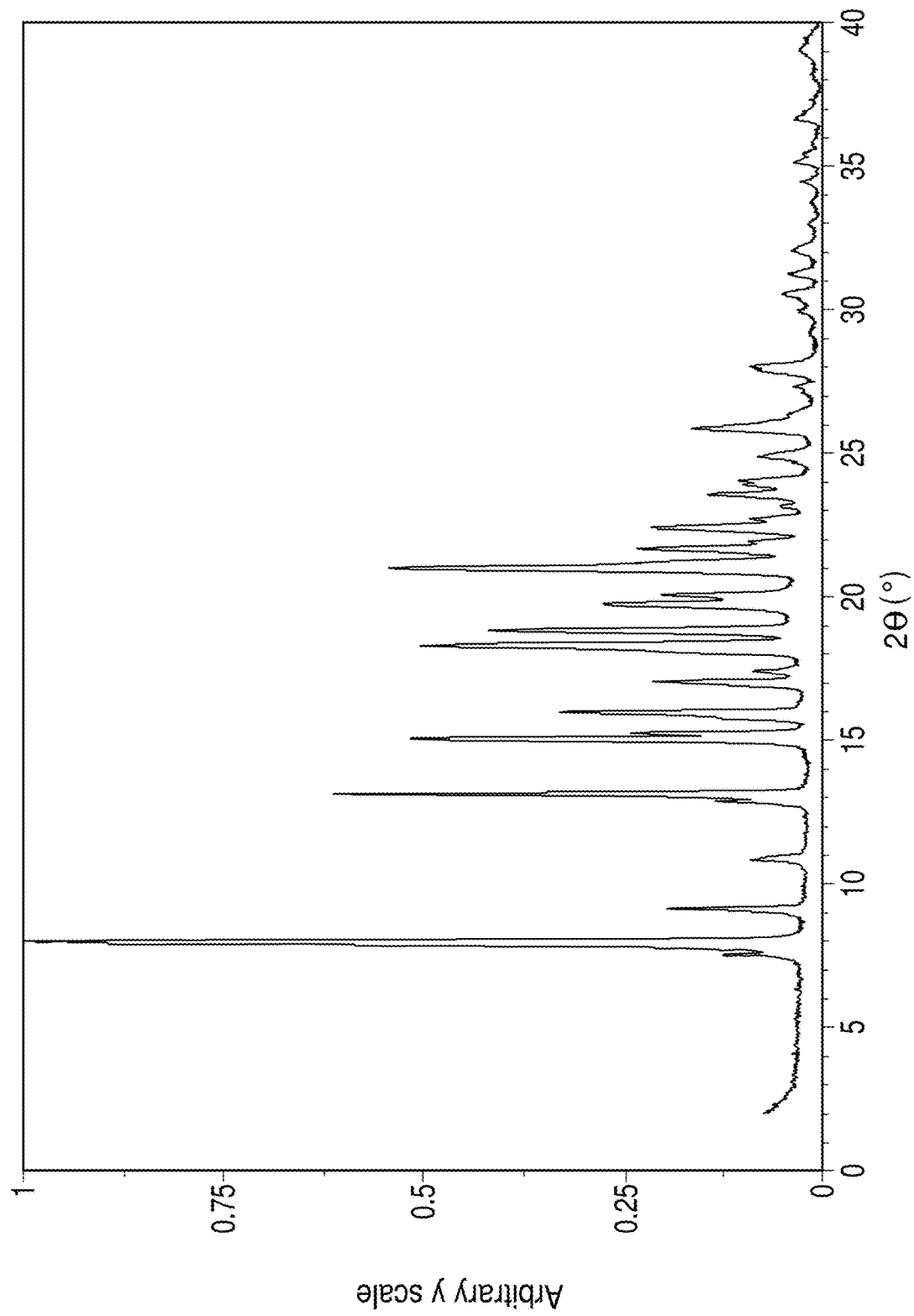

The present disclosure relates to novel methods of making a crystal form of ritonavir known as ritonavir Form III, and methods of using the product produced by the method, and pharmaceutical compositions comprising the product produced by the provided method.

Ritonavir is known to have utility for the inhibition of HIV protease, the inhibition of HIV infection, the inhibition of cytochrome P450 monooxygenase and the enhancement of the pharmacokinetics of compounds which are metabolized by cytochrome P450 monooxygenase. ritonavir is particularly effective for the inhibition of HIV infection when used alone or in combination with one or more reverse transcriptase inhibitors and/or one or more other HIV protease inhibitors.

During the development and initial manufacture of ritonavir, only one crystal form was identified. Bauer, J., et al., *Pharm. Res.*, 2001, 18(6):859-866. Because ritonavir is not bioavailable in that form, however, the initially marketed oral formulations that comprised it contained ritonavir dissolved in a semi-solid, waxy matrix filled into capsules. About two years after the initial marketing of NORVIR®, a second crystal form of ritonavir was discovered; its presence in the capsule formulation caused the product to fail the dissolution specification mandated by the regulatory agencies. Id. As it later turned out, this new form, which is referred to as "Form II," was supersaturated in the hydroalcoholic solutions used in the drug formulations, even though the originally known form, which is now referred to as "Form I," was not. The sudden appearance of the significantly less soluble Form II prevented the further manufacture of the original NORVIR® formulations, and seriously threatened the supply of the drug. Id. At some considerable cost, a new formulation of NORVIR® was eventually developed.

Until recently, there were three reported polymorphs (same chemical composition) of ritonavir. Forms I and II are as described in U.S. Pat. No. 7,148,359 ("US'359"), and a third form obtained by Morissette et al. first described as "Form V" ritonavir in U.S. Pat. No. 7,205,413 ("US'413") but later described as "Form IV" ritonavir as published in Morissette et al. *PNAS*, 2003, 100 (5) 2180-2184. ("Morissette 2003"). This form will be referred to as "Form IV ritonavir" herein.

Most recently, researchers from AbbVie Inc. published a rapid communication reporting the discovery of a new anhydrous form, "Form III" ritonavir. Yao, X., et al., ("Yao 2022"). Although, this form appears to have been observed by Kawakami et al. *Molecular Pharmaceutics*, 2014, 11(6): p. 1835-1843.

An overlay provided herein of the Form III ritonavir X-ray powder diffraction (XRPD) pattern published by AbbVie and the ritonavir XRPD patterns in the 2014 publication by Kawakami et al. (See FIG. 2) shows that Kawakami's labeled "Form IV" ritonavir was actually a mixture of the AbbVie Form III ritonavir (Yao, 2022) and amorphous ritonavir, although that appears to have been unrecognized by Kawakami et al.

A need exists for more consistent and rapid methods of making crystalline Form III ritonavir, which has promising bioavailable properties.

2. SUMMARY

Coincidentally, at the same time as AbbVie's publication (i.e., Yao, 2022), the present inventors were also investigating ritonavir, and simultaneously discovered the same Form III ritonavir via an improved method. The present disclosure provides a simple thermal method to generate Form III in less time than previously reported and that can be easily performed terrestrially or in reduced gravity.

In some aspects of the disclosure, methods for obtaining Form III ritonavir are provided comprising melting a sample of Form H ritonavir; cooling the sample to a first temperature within a nucleation temperature range for a nucleation period to obtain Form III ritonavir.

In certain embodiments, the method further comprises holding the temperature at the first temperature for a nucleation period; and optionally ramping the sample from the first temperature to a second temperature; wherein the first and second temperatures are within the nucleation temperature range.

In additional aspects of the disclosure, Form III ritonavir made by the methods herein is described.

In certain embodiments, the obtained Form III ritonavir comprises a mixture of amorphous ritonavir and Form III ritonavir.

In further aspects of the disclosure, pharmaceutical compositions are provided comprising Form III ritonavir and one or more pharmaceutically acceptable excipients.

In still further aspects of the disclosure, methods of treating disease such as HIV, COVID-19 and/or diseases related to the inhibition of cytochrome P450-3A4 are provided comprising treating a patient in need with a therapeutically effective amount of Form III ritonavir such as with a pharmaceutical composition of Form III ritonavir.

In an embodiment of the present disclosure, a method for obtaining Form III ritonavir is provided, comprising the steps of melting a sample of ritonavir; cooling the sample to a first temperature within a nucleation temperature range for a nucleation period; and obtaining Form III ritonavir.

In certain embodiments, the method further comprises: holding the temperature at the first temperature for a nucleation period; and optionally ramping the sample from the first temperature to a second temperature; wherein the first and second temperatures are within the nucleation temperature range.

In certain embodiments, the nucleation temperature range is from above 60° C. to about 100° C.

In certain embodiments, the obtained Form III ritonavir forms within the nucleation temperature range.

In certain embodiments, the X-ray powder diffraction pattern of Form III ritonavir comprises peaks at about 7.9° and about 9.1°. In certain embodiments, the X-ray powder diffraction pattern of Form III ritonavir further comprises one or more peaks at about 7.5°, 10.8°, about 13.1°, about 15.0°, about 15.9°, about 17.0°, about 18.2°, about 18.8°, and about 20.1°.

In certain embodiments, the differential scanning calorimetry thermogram of Form III ritonavir has an endotherm with an onset temperature of about 114° C.

In certain embodiments, the form of the ritonavir sample to be melted is selected from amorphous ritonavir, Form I ritonavir, Form II ritonavir, or Form IV ritonavir. In certain embodiments, the form of the ritonavir sample to be melted is selected from amorphous ritonavir, Form I ritonavir, or Form II ritonavir. In certain embodiments, the form of the ritonavir sample to be melted is selected from amorphous ritonavir or Form I ritonavir. In certain embodiments, the form of the ritonavir sample to be melted is selected from amorphous ritonavir or Form II ritonavir. In certain embodiments, the form of the ritonavir sample to be melted is Form I ritonavir.

In certain embodiments, melting comprises ramping the temperature of the sample to a melt temperature of 125° C. or greater. In certain embodiments, the melt temperature is between about 125° C. to about 128° C.

In certain embodiments, the melt temperature is above the melting point of Form II ritonavir and held until the entire sample is melted. In certain embodiments, the melt temperature is above the melting point of Form II ritonavir and held until no crystalline particles are visible. In certain embodiments, the melt temperature is above the melting point of Form II ritonavir and held until no seed crystals of Form II are present in the melt.

In certain embodiments, the melt temperature is held for at least two minutes. In certain embodiments, the melt temperature is held for at least 15 minutes. In certain embodiments, the melt temperature is held between about 15 minutes and about 30 minutes.

In certain embodiments, the nucleation period is between 1 hour and 48 hours. In certain embodiments, the nucleation period is about 23 hours. In certain embodiments, the nucleation period is about 37 hours.

In certain embodiments, crystallization of the sample is substantially complete during the nucleation period. In certain embodiments, the nucleation period is until the conversion from Form II ritonavir to Form III ritonavir in the sample is substantially complete.

In certain embodiments, the methods provided by the present disclosure further comprise the step of cooling the obtained Form III ritonavir. In certain embodiments, the obtained Form III ritonavir is cooled to a temperature below the glass transition temperature of amorphous ritonavir.

In certain embodiments, the amount of sample to be melted is between about 0.5 mg and about 300 mg.

In certain embodiments, the sample is confirmed to be melted by the absence of any crystalline material as observed by hot stage optical microscopy (HSOM).

In certain embodiments, the crystalizing is performed under reduced gravity conditions.

In certain embodiments, the reduced gravity conditions occur in a spacecraft in orbit around the Earth.

In another aspect, Form III ritonavir is provided as prepared by the methods of the present disclosure.

In another aspect, a pharmaceutical composition is provided comprising Form III ritonavir is provided as prepared by the methods of the present disclosure and one or more pharmaceutically acceptable excipients.

In another aspect, a method of treating one or more of HIV or COVID-19 is provided comprising administering to a patient need thereof a pharmaceutically acceptable amount of Form III ritonavir is provided as prepared by the methods of the present disclosure.

In another aspect, a method of inhibiting cytochrome P450-3A4 is provided comprising administering to a patient need thereof a pharmaceutically acceptable amount of Form III ritonavir is provided as prepared by the methods of the present disclosure.

3. BRIEF DESCRIPTION OF THE DRAWINGS

These and other features, aspects, and advantages of the present disclosure will become better understood with regard to the following description, and accompanying drawings, where:

FIG. 1 provides an X-ray powder diffraction (XRPD) pattern for Form III ritonavir of example 1f.

Figure 2:
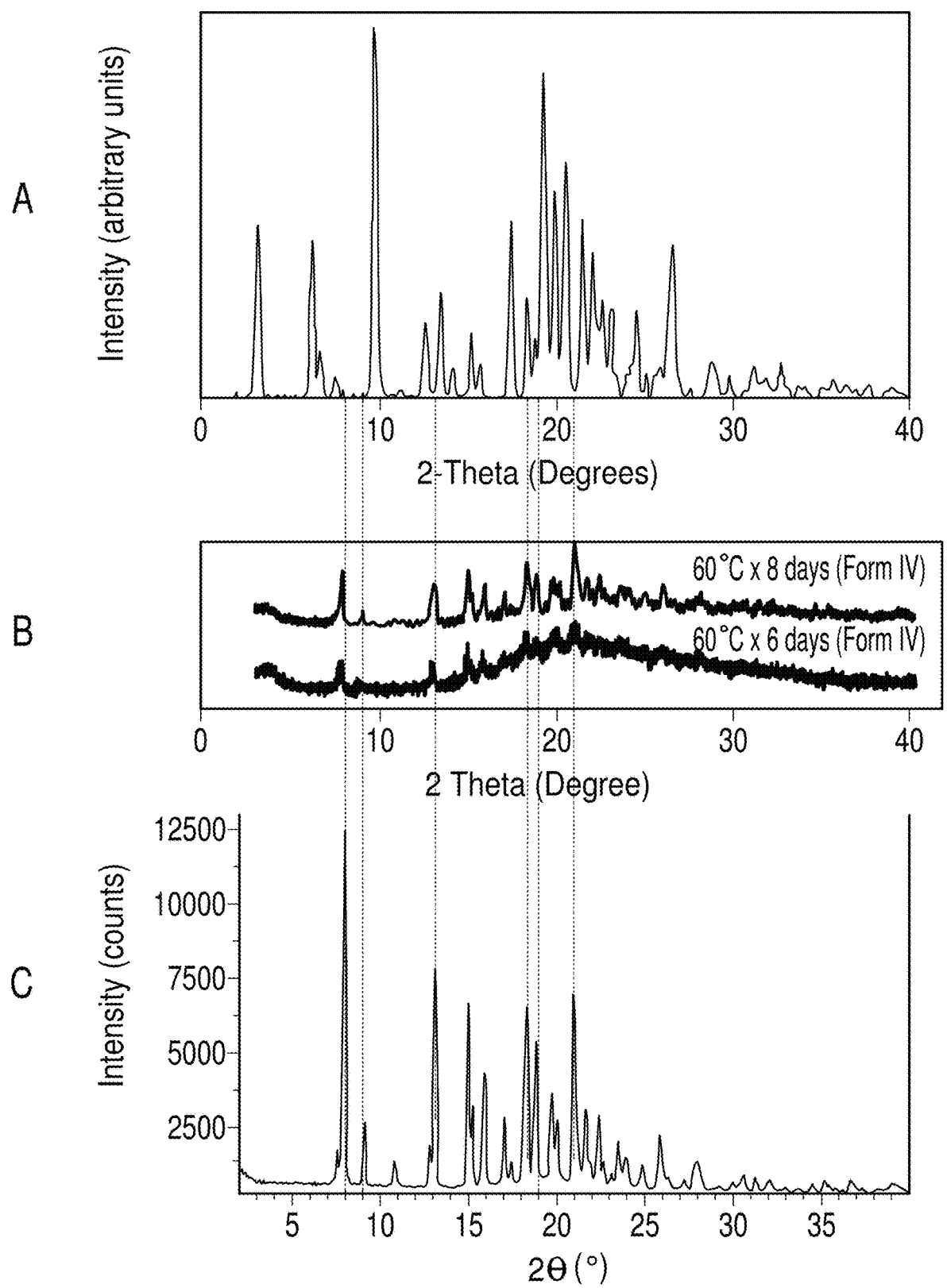

FIG. 2, panels A-C, show a comparison of XRPD patterns corresponding to Form IV ritonavir reported by Morissette et al. (top XRPD pattern) (panel A), Kawakami's "Form IV" after heating at 60° C. for 6 and 8 days (panel B), and Form III ritonavir of the present disclosure (panel C). The three XRPD patterns are presented with the x-axes (° 2θ) on the same scale, and with vertical dotted lines corresponding to peaks of the Form III ritonavir of the disclosure to facilitate comparison of peaks between the various XRPD patterns reported for other Forms of ritonavir.

Figure 3:
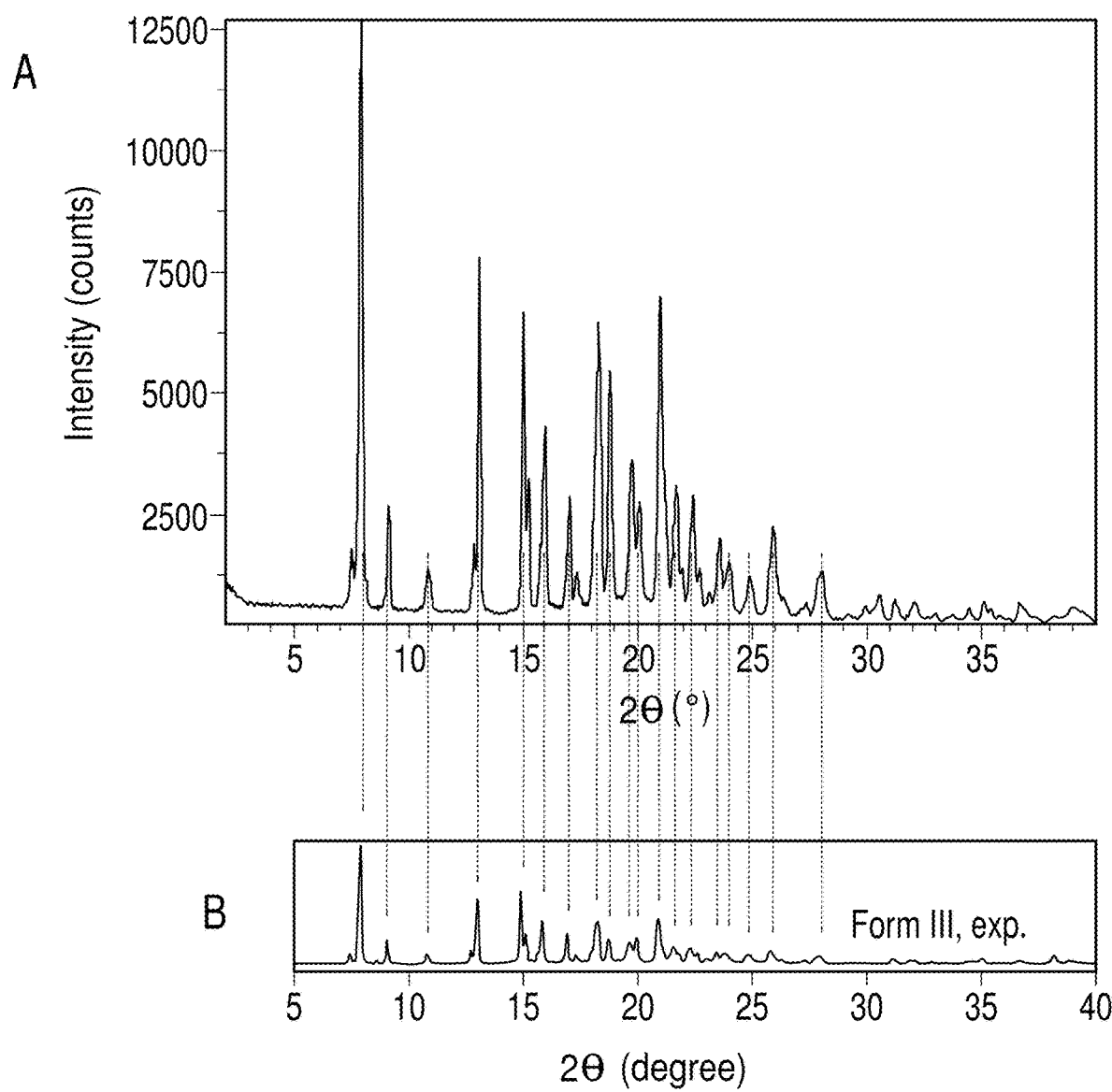

FIG. 3, panels A-B, show a comparison of XRPD pattern of Form III ritonavir of the present disclosure (top) and the XRPD pattern of the Yao et al., 2022.

Figure 4:
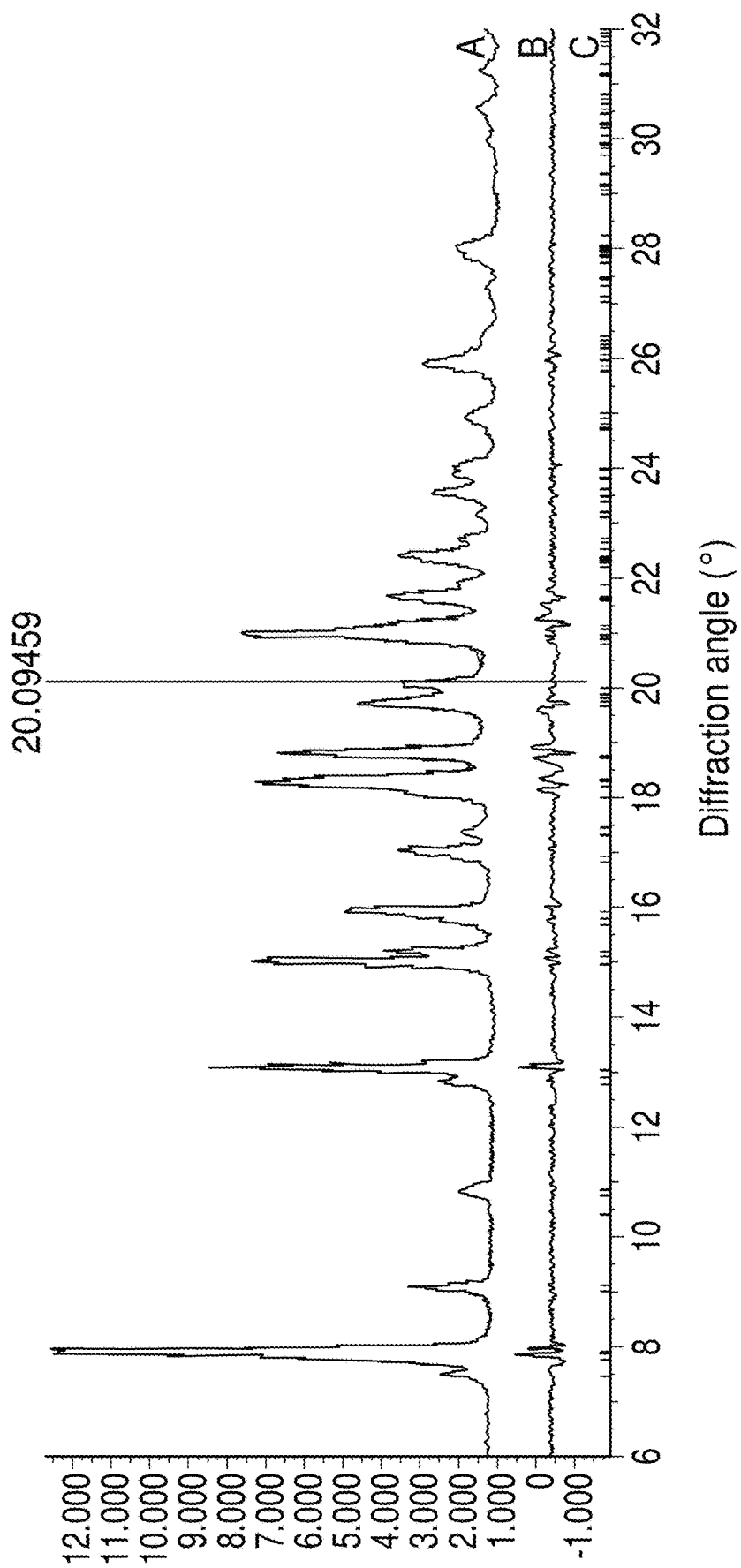

FIG. 4 provides evidence confirming the identification of the presently obtained material as Form III ritonavir. FIG. 4, line A shows the substantial overlap of two XRPD patterns of Form III ritonavir. Line A is an experimentally obtained XRPD pattern of Form III ritonavir of the present disclosure (example 1f) and the other results from the indexing solution of that XRPD pattern, including a Pawley refinement, line C. The goodness of fit is represented in FIG. 4, line B, which is the difference between the XRPD patterns. The intensity of the differences is small compared to the size of most peaks, demonstrating relatively high goodness of fit. In FIG. 4, line C all of the allowed peaks from the indexing solution, post Pawley refinement, are presented.

Figure 5:
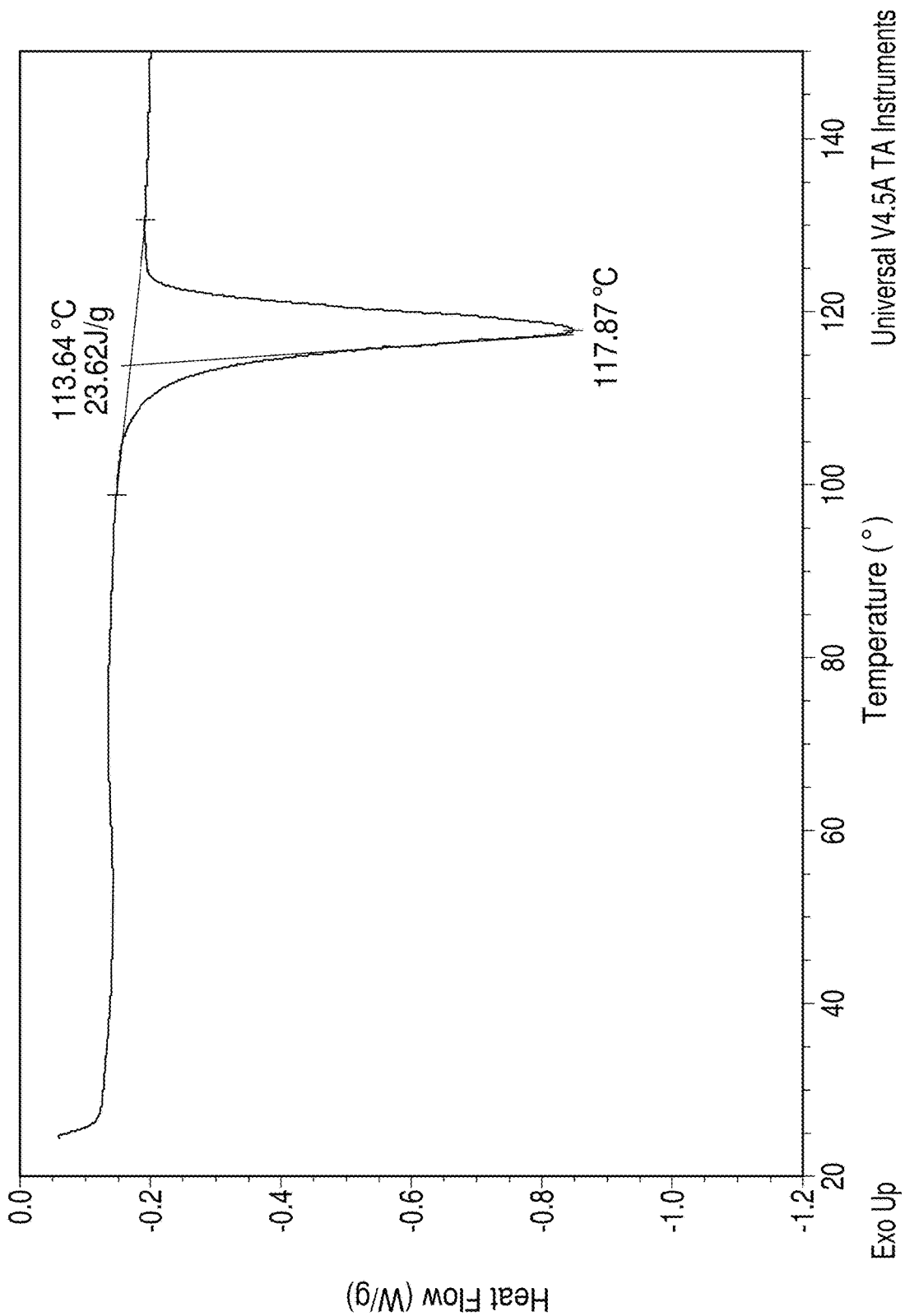

FIG. 5 provides a Differential Scanning Calorimetry (DSC) Thermogram for Form III ritonavir obtained as described in example 1f, wherein the endotherm is approximately 23.62 J/g.

Figure 6B:
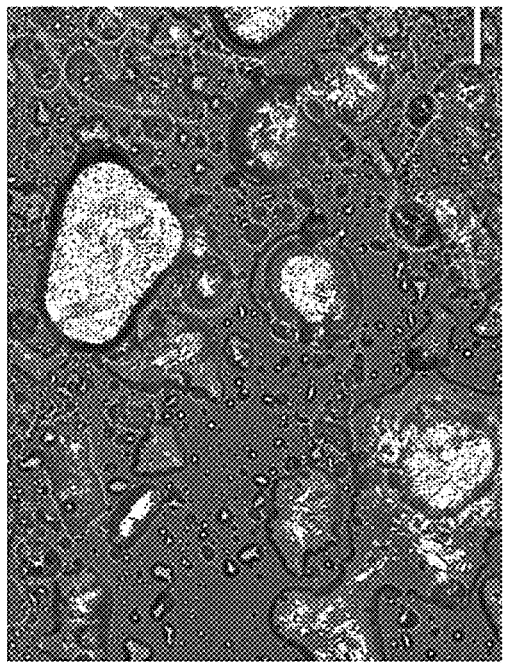
Figure 6D:
Figure 6A:
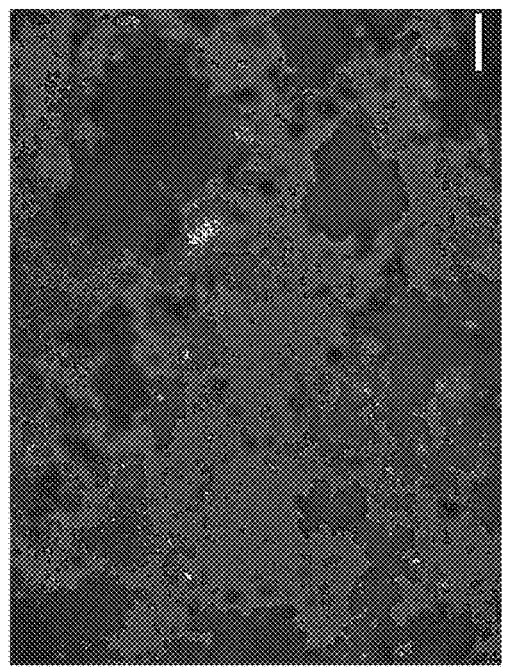
Figure 6C:
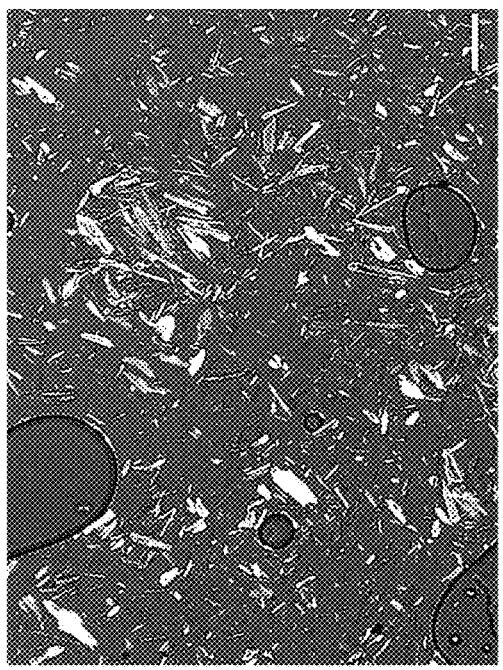

FIGS. 6A-6D provide several HSOM images of a sample of Form III ritonavir obtained as described in example 1f. FIG. 6A) the melt onset at 113.7° C.; FIG. 6B) continued melting at 115.8° C.; FIG. 6C) continued melting at 117.0° C.; FIG. 6D) melt completion by 117.9° C.

Figure 7:
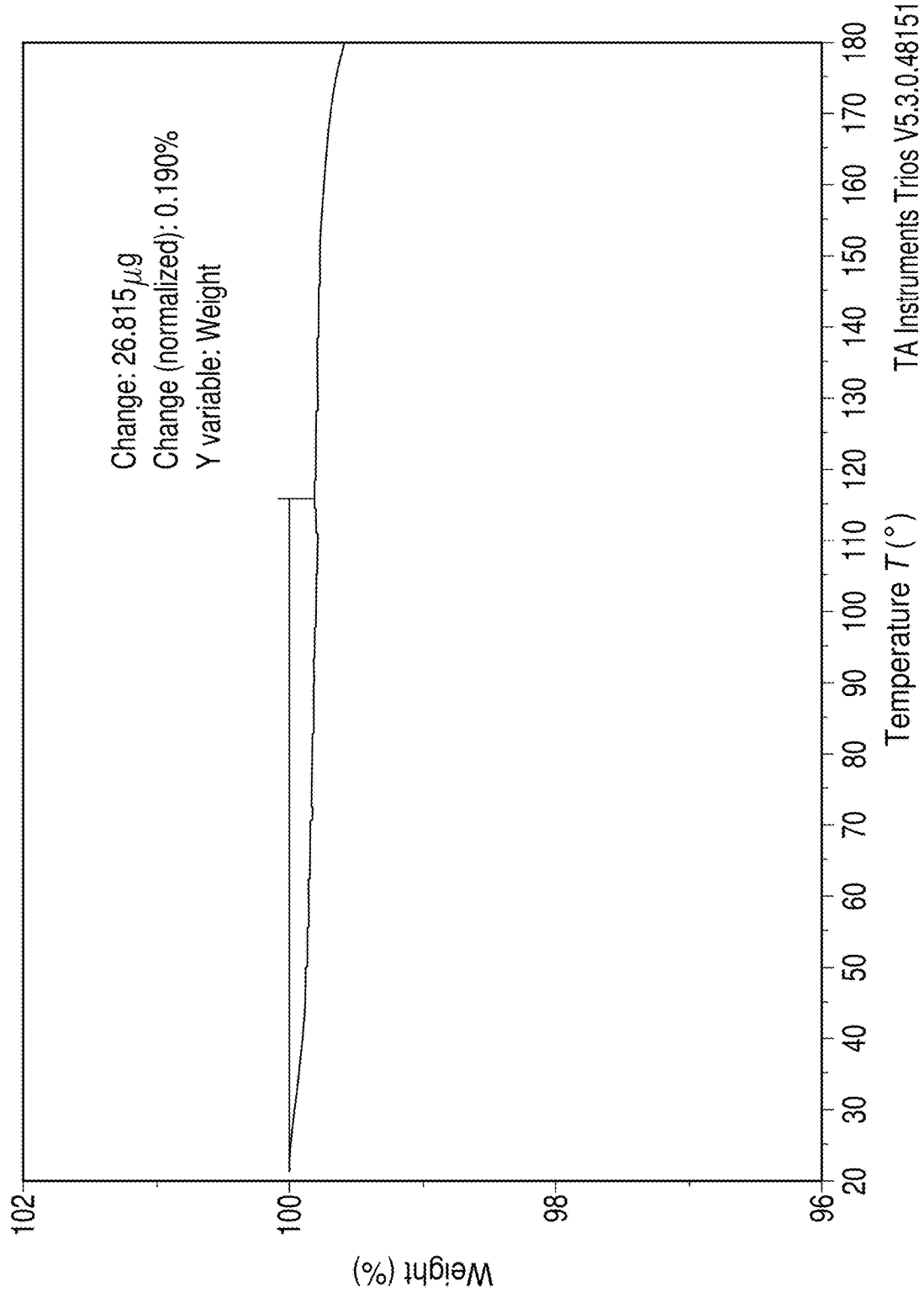

FIG. 7 provides a thermogravimetric (TG) curve for Form III ritonavir obtained as described in example 1f.

Figure 8:
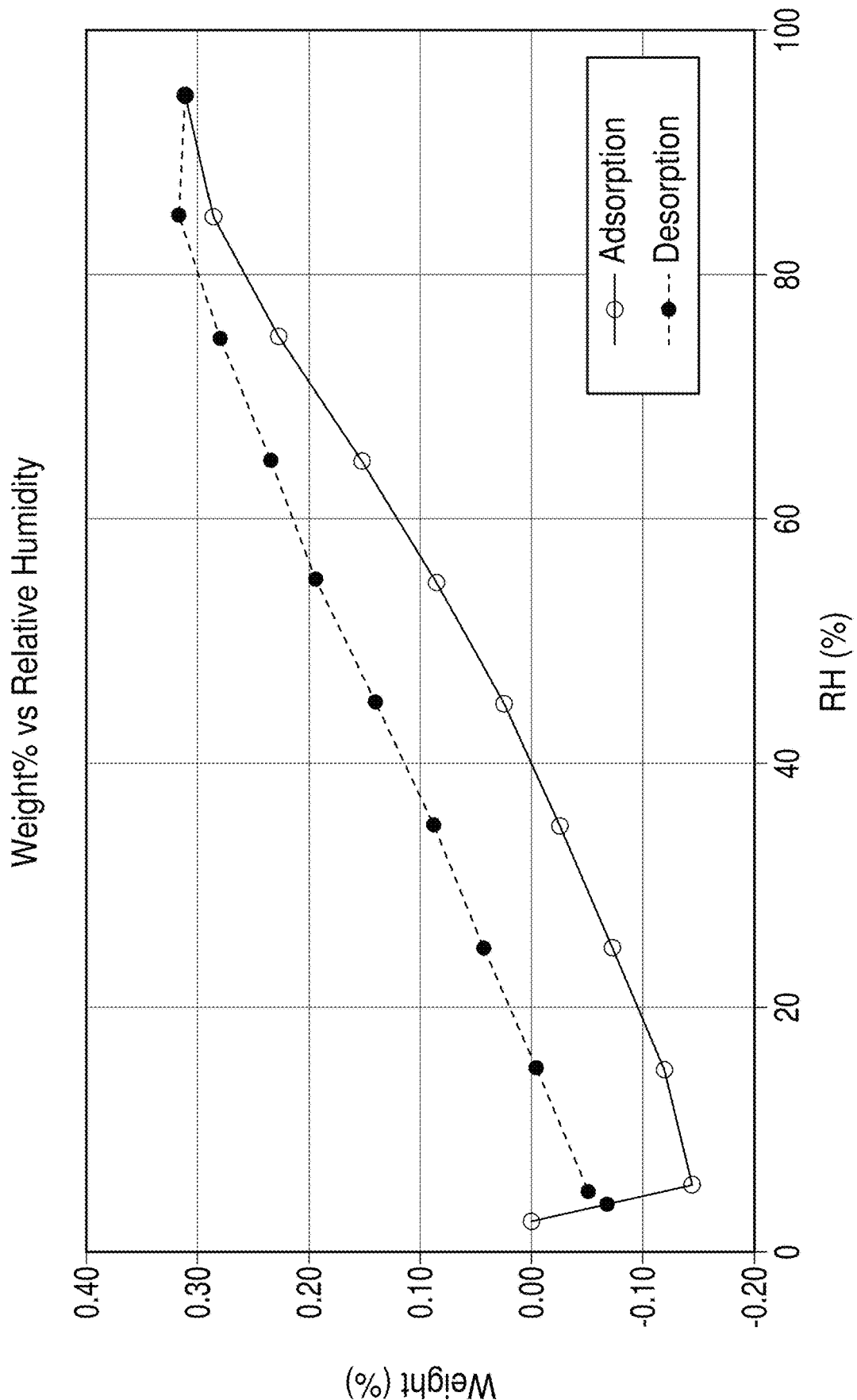

FIG. 8 provides a DVS (dynamic vapor sorption) isotherm for Form III ritonavir obtained as described in example 1f.

Figure 9A:
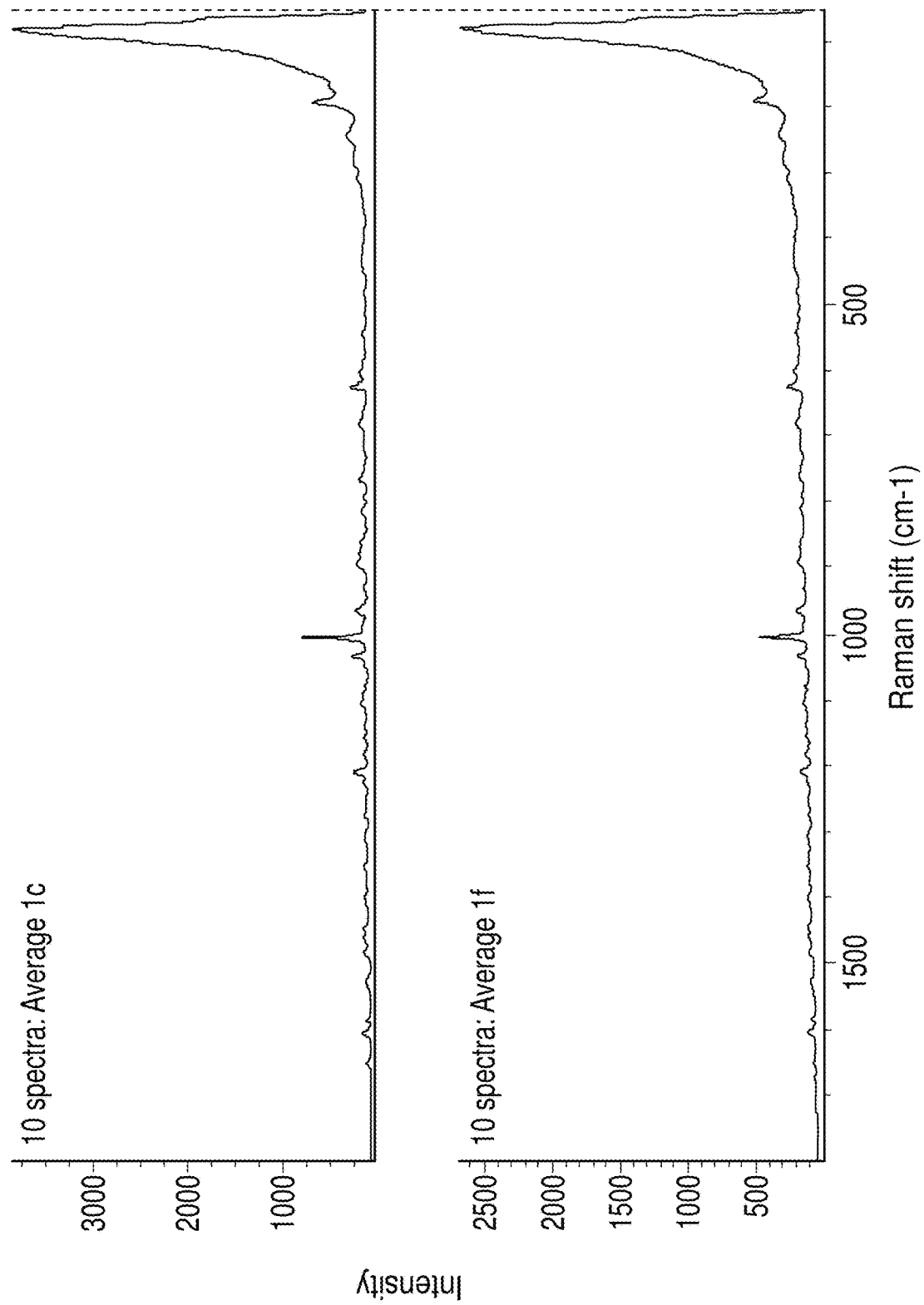
Figure 9B:
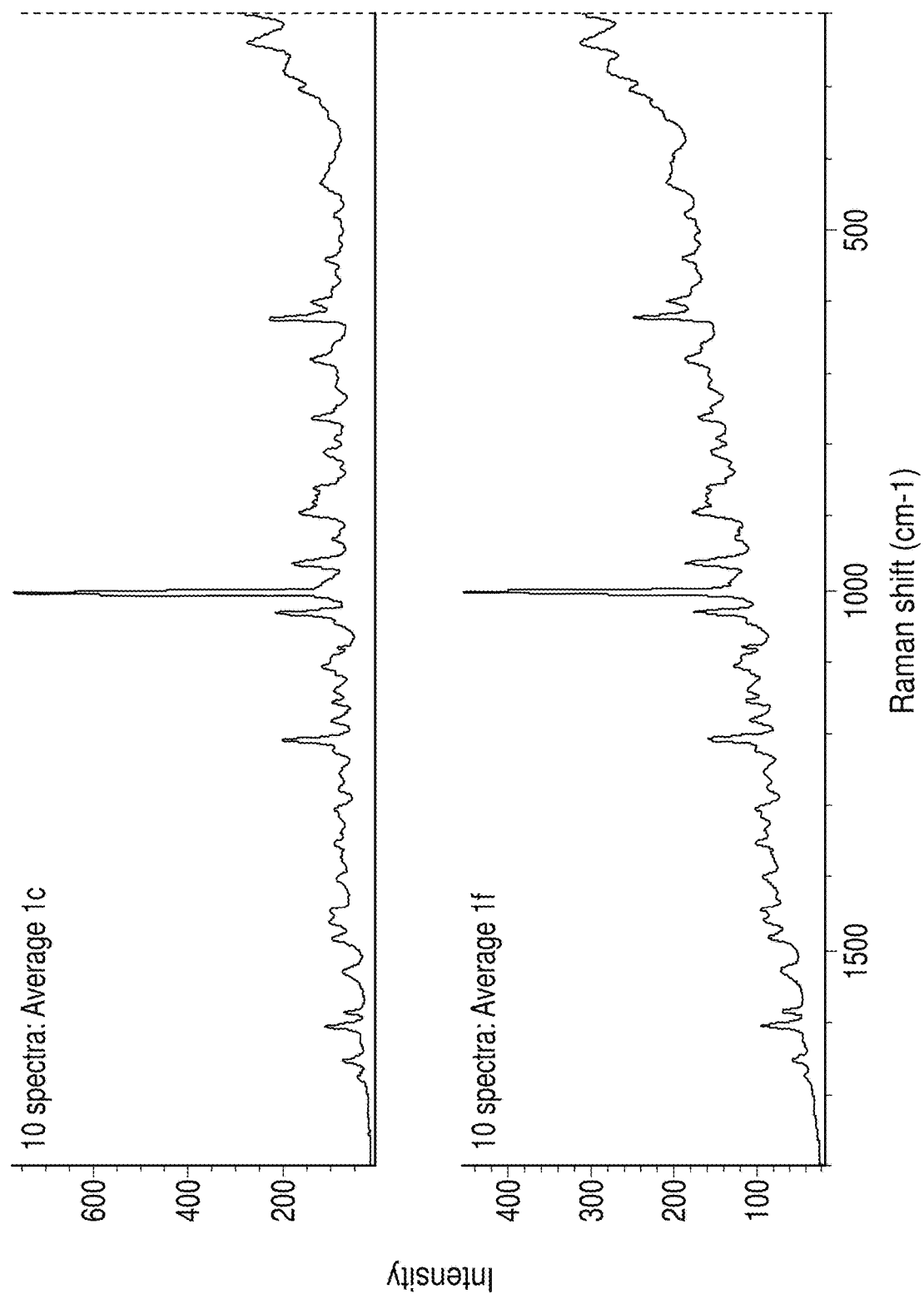

FIGS. 9A-9B provide Raman spectra of Form III ritonavir obtained as described in example 1f: FIG. 9A) provides the full spectral range, and FIG. 9B) provides a zoomed-in view.

Figure 10A:
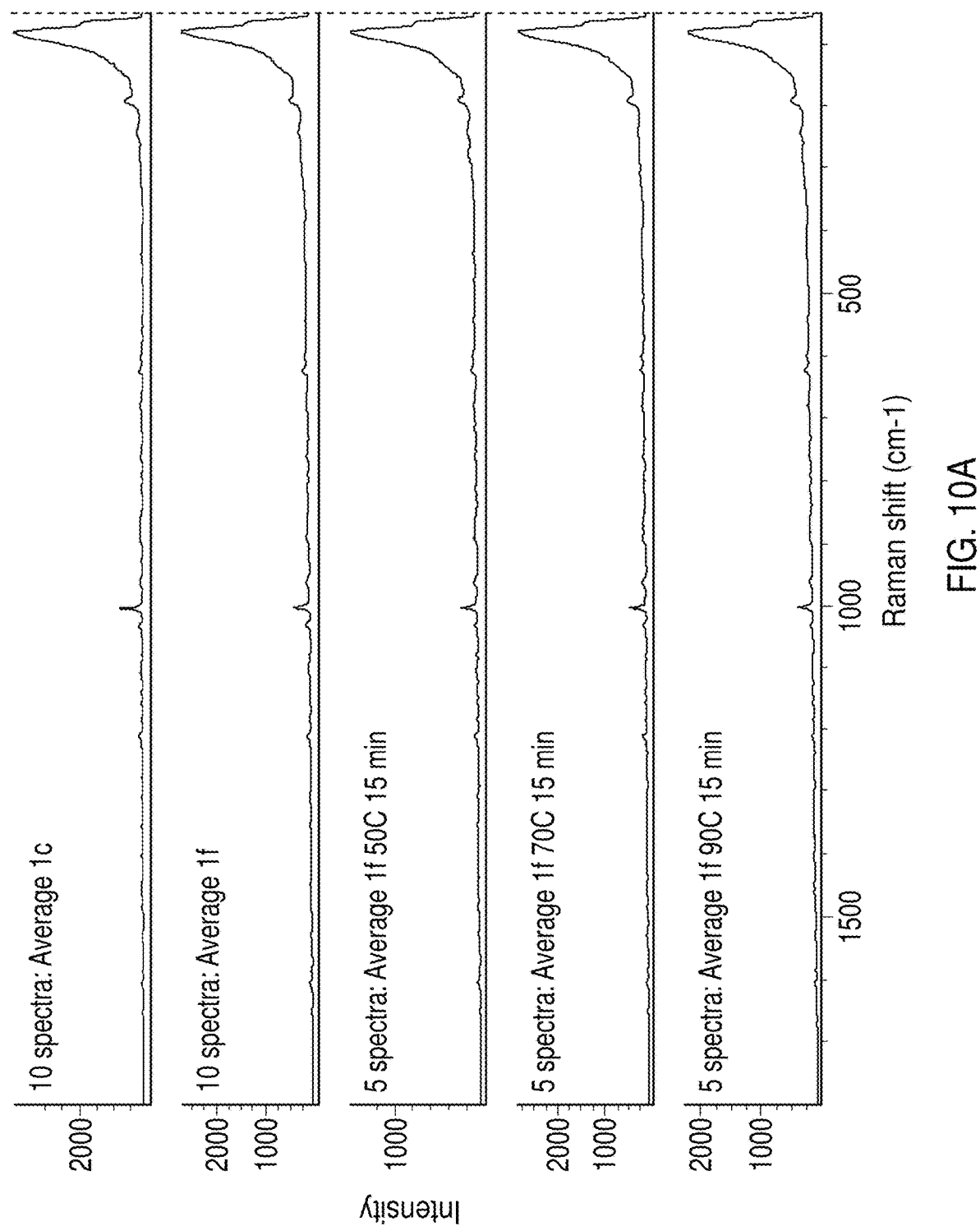
Figure 10B:
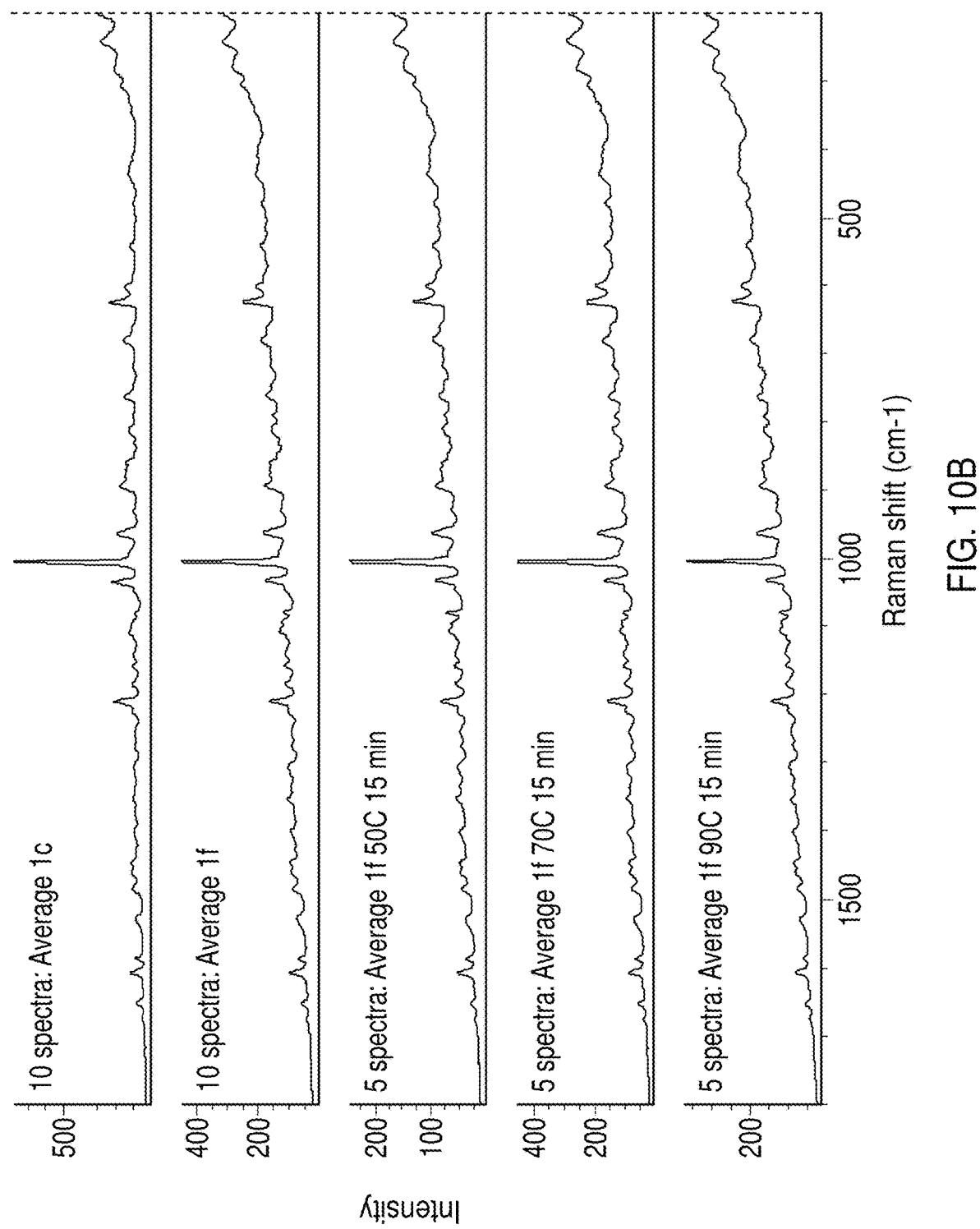

FIGS. 10A-10B provide Raman spectra of Form III ritonavir short-term stability results of example 1f: FIG. 10A) provides the full spectral range, FIG. 10A) provides a zoomed-in view.

Figure 11A:
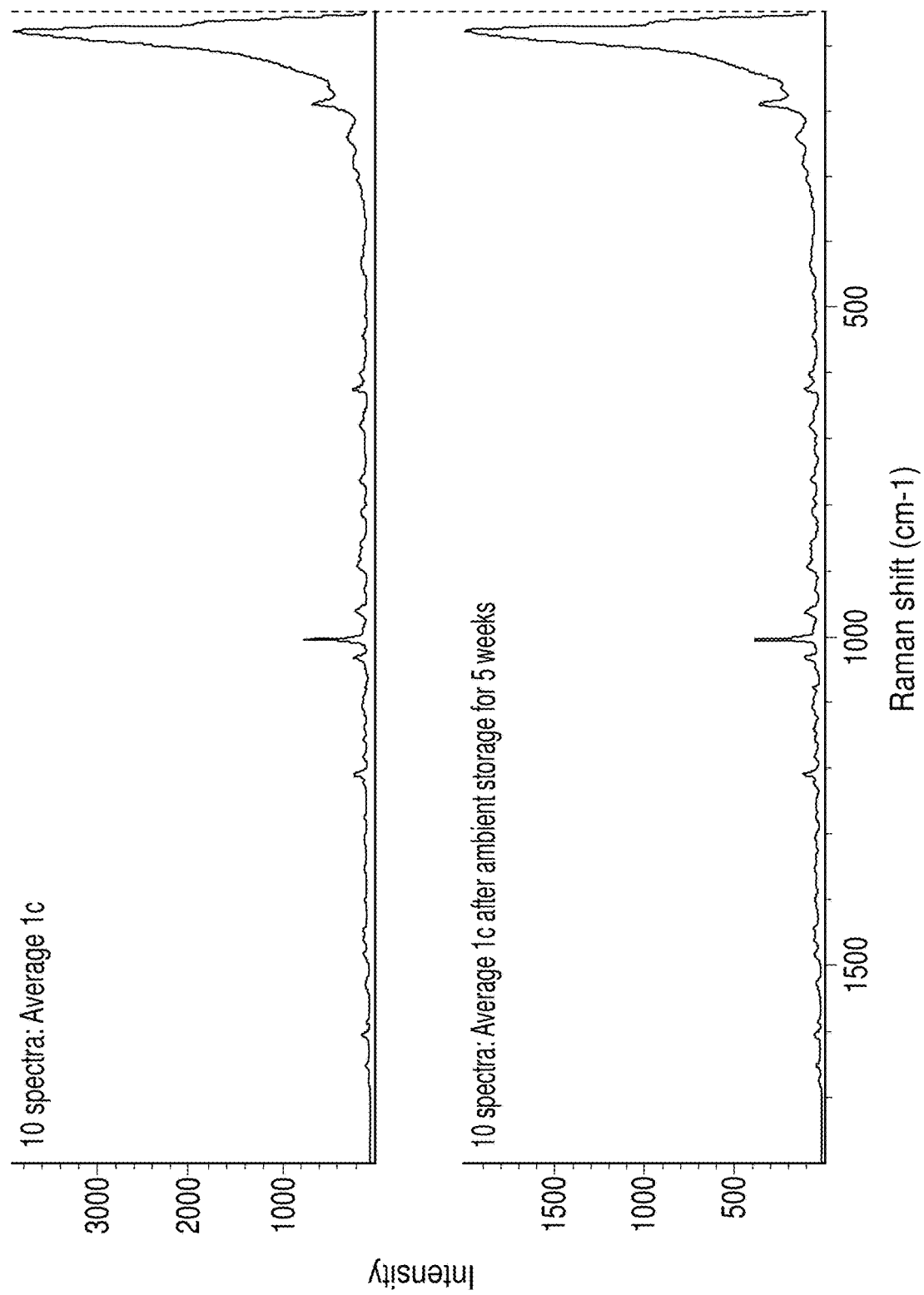
Figure 11B:
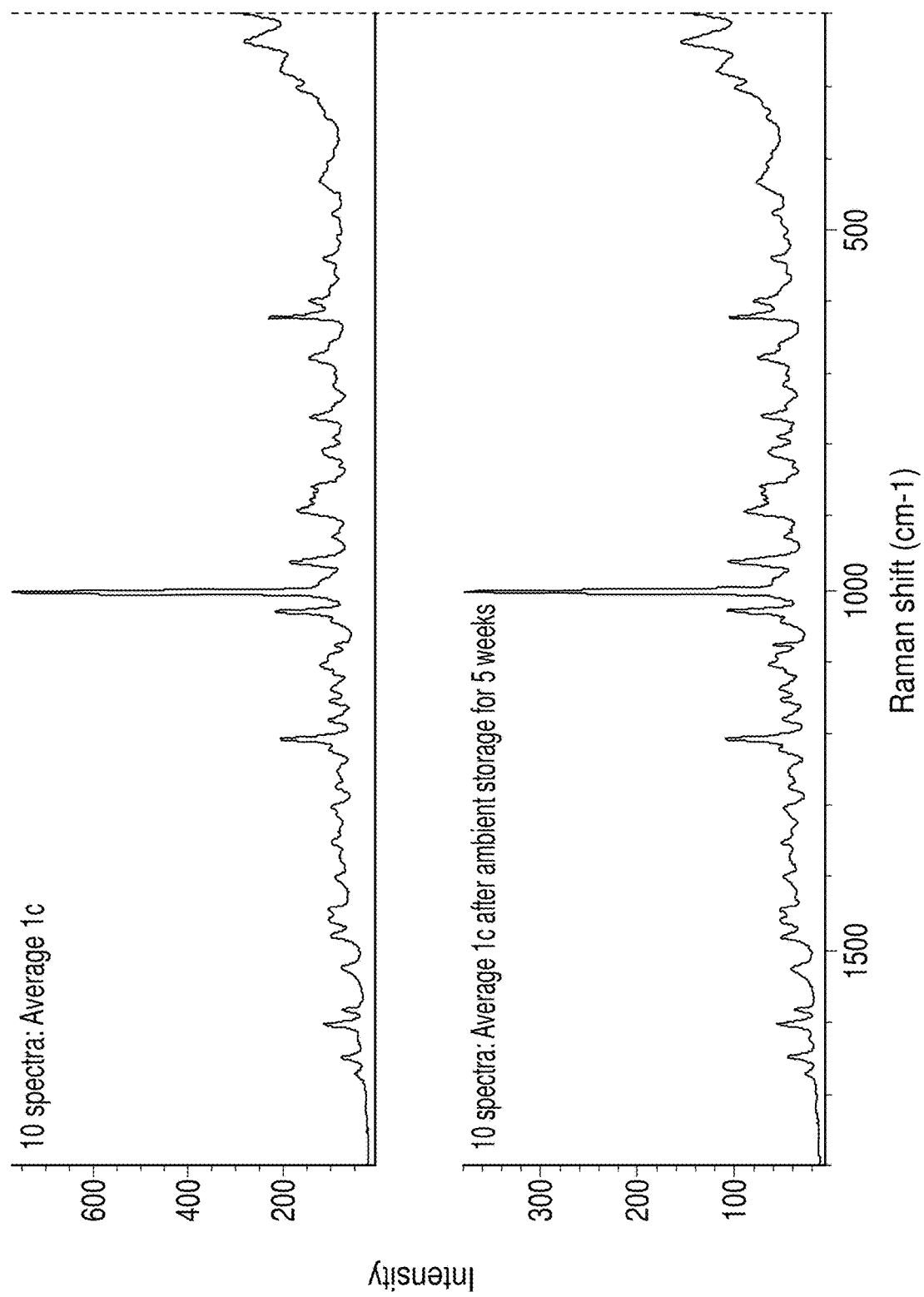
Figure 11C:
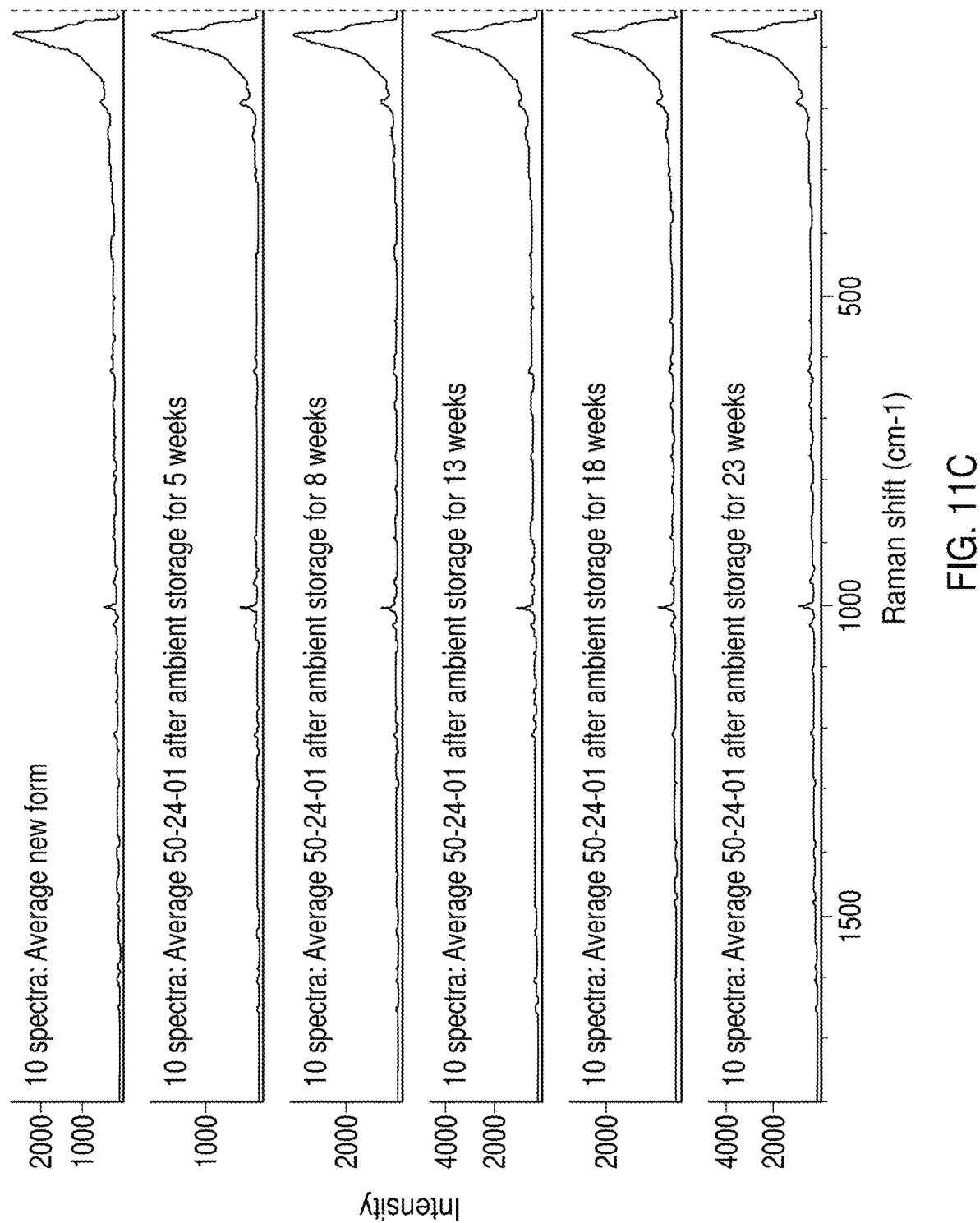
Figure 11D:
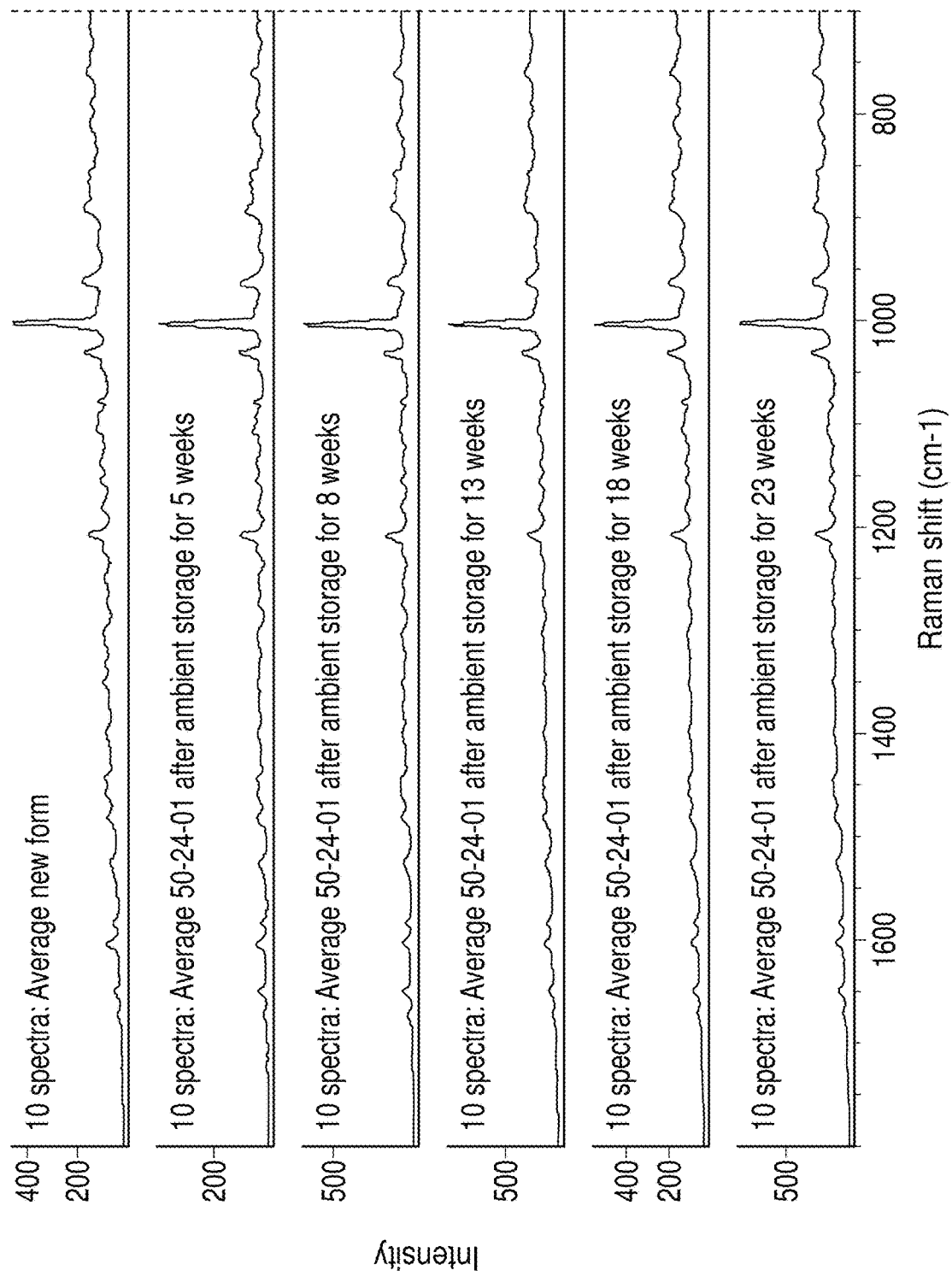

FIGS. 11A-11D provide Raman spectra of Form III ritonavir at 5-week and 23-weeks stability study described in Example 1c. FIGS. 11A-11B provide Raman spectra of Form III ritonavir 5-week stability results of example 1c: FIG. 11A) full spectral range, FIG. 11B) zoomed-in view. FIGS. 11C-11D provide Raman spectra of Form III ritonavir 23-week stability results of example 1c: FIG. 11C) full spectral range, FIG. 11D) zoomed-in view.

Figure 12A:
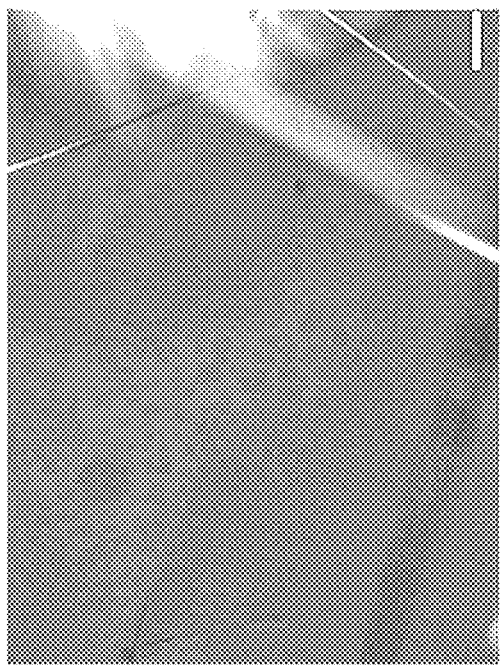
Figure 12B:
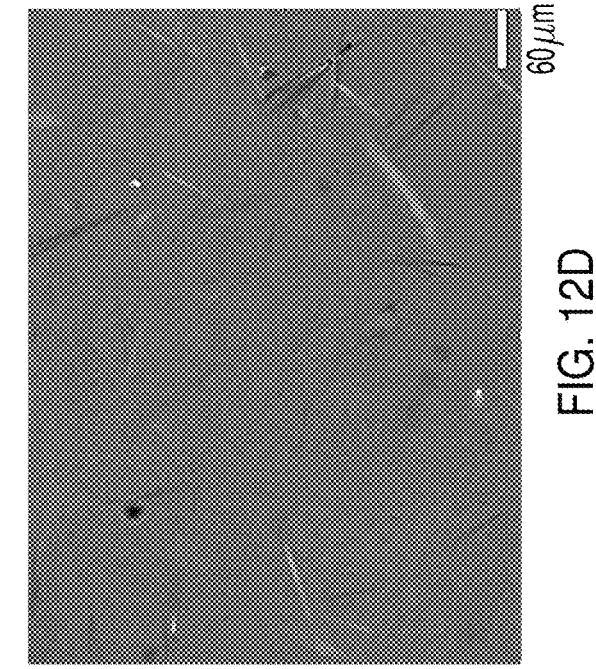
Figure 12C:
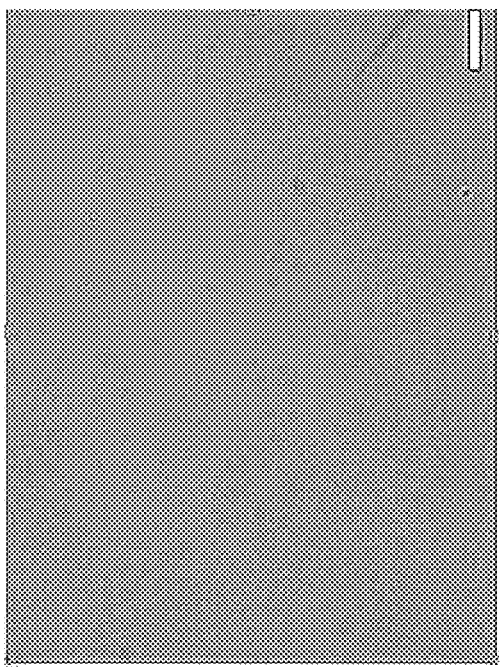
Figure 12D:
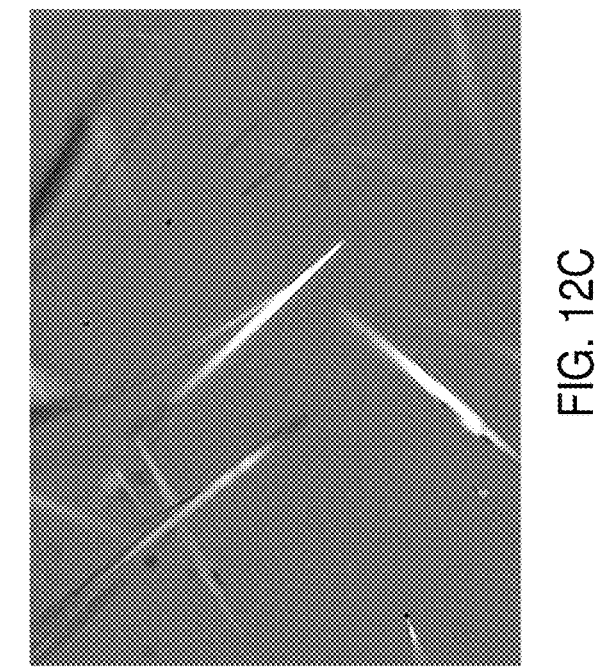
Figure 12E:
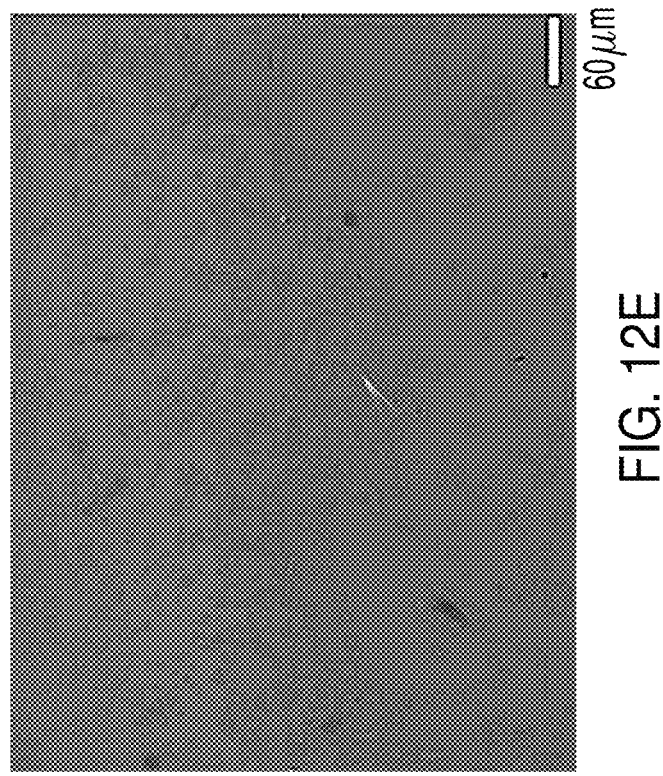

FIGS. 12A-12E provide HSOM images of Form III ritonavir crystals grown from supercooled melts when held for 5 hours at: FIG. 12A) 90° C.; FIG. 12B) 85° C.; FIG. 12C) 80° C.; FIG. 12D) 75° C.; and FIG. 12E) 70° C.

Figure 13B:
Figure 13A:
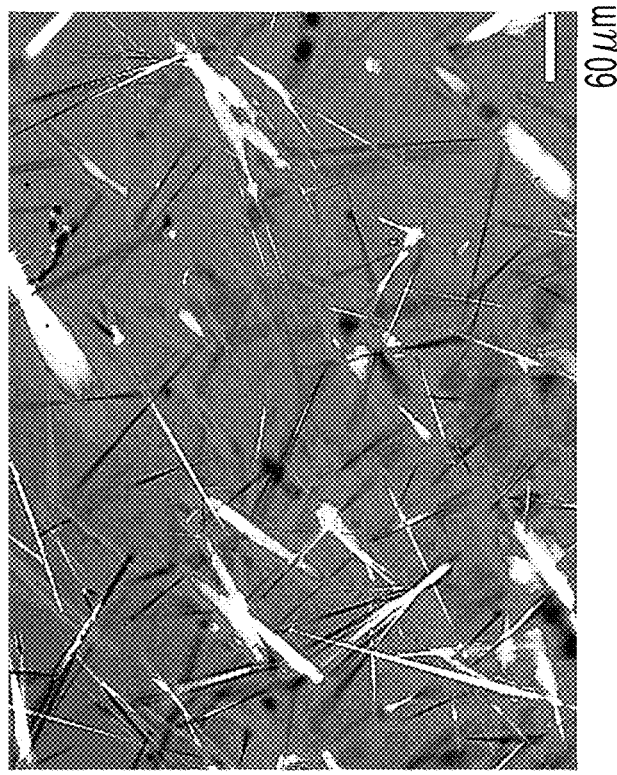

FIGS. 13A-13B provide the HSOM images of Form III ritonavir crystals grown at 80° C. from the supercooled melt after FIG. 13A) 5 hours; FIG. 13B) 8 hours.

Figure 14:
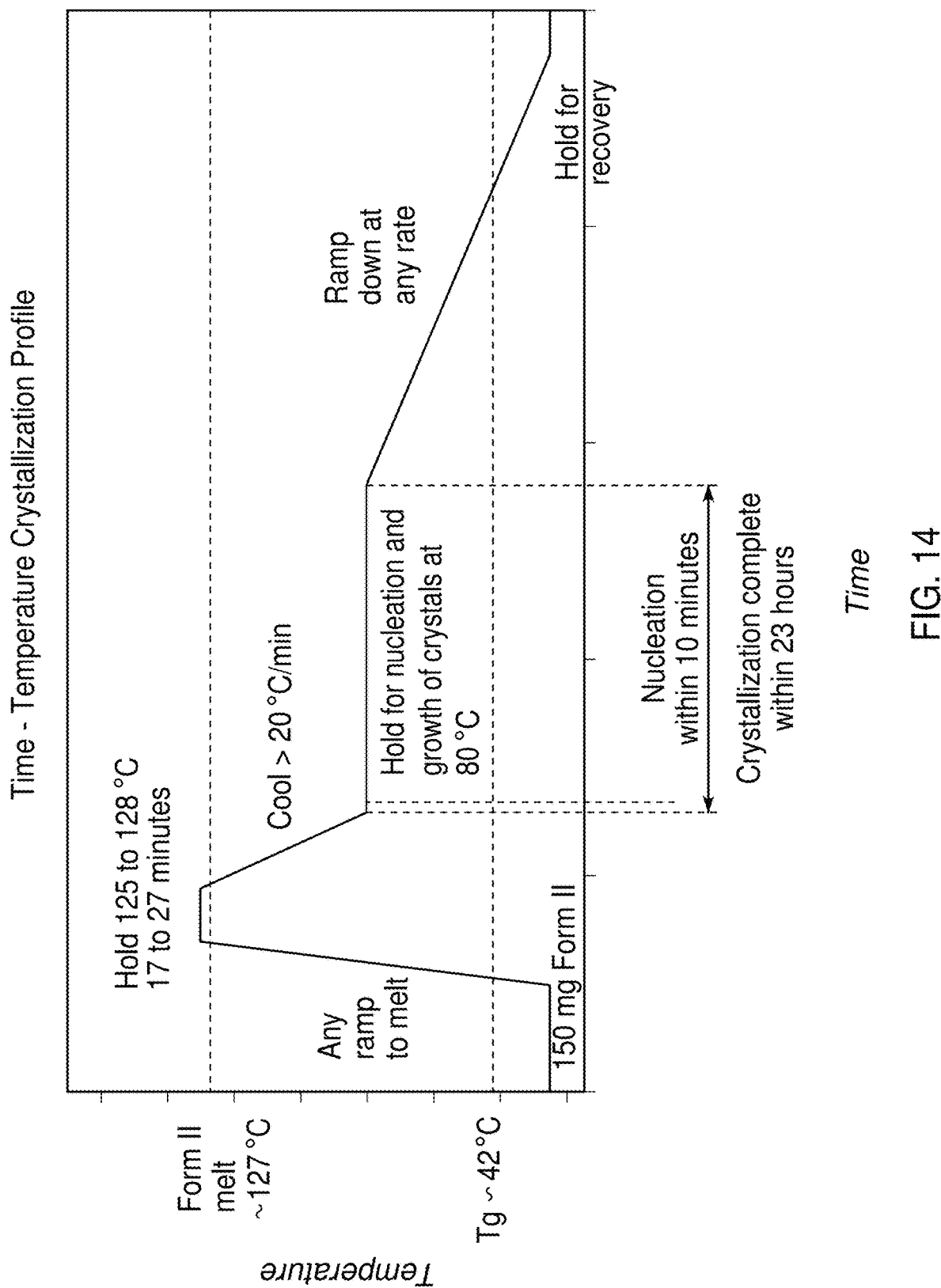

FIG. 14 provides a temperature profile used to provide Form III ritonavir from a supercooled melt within 23 hours.

Figure 15:
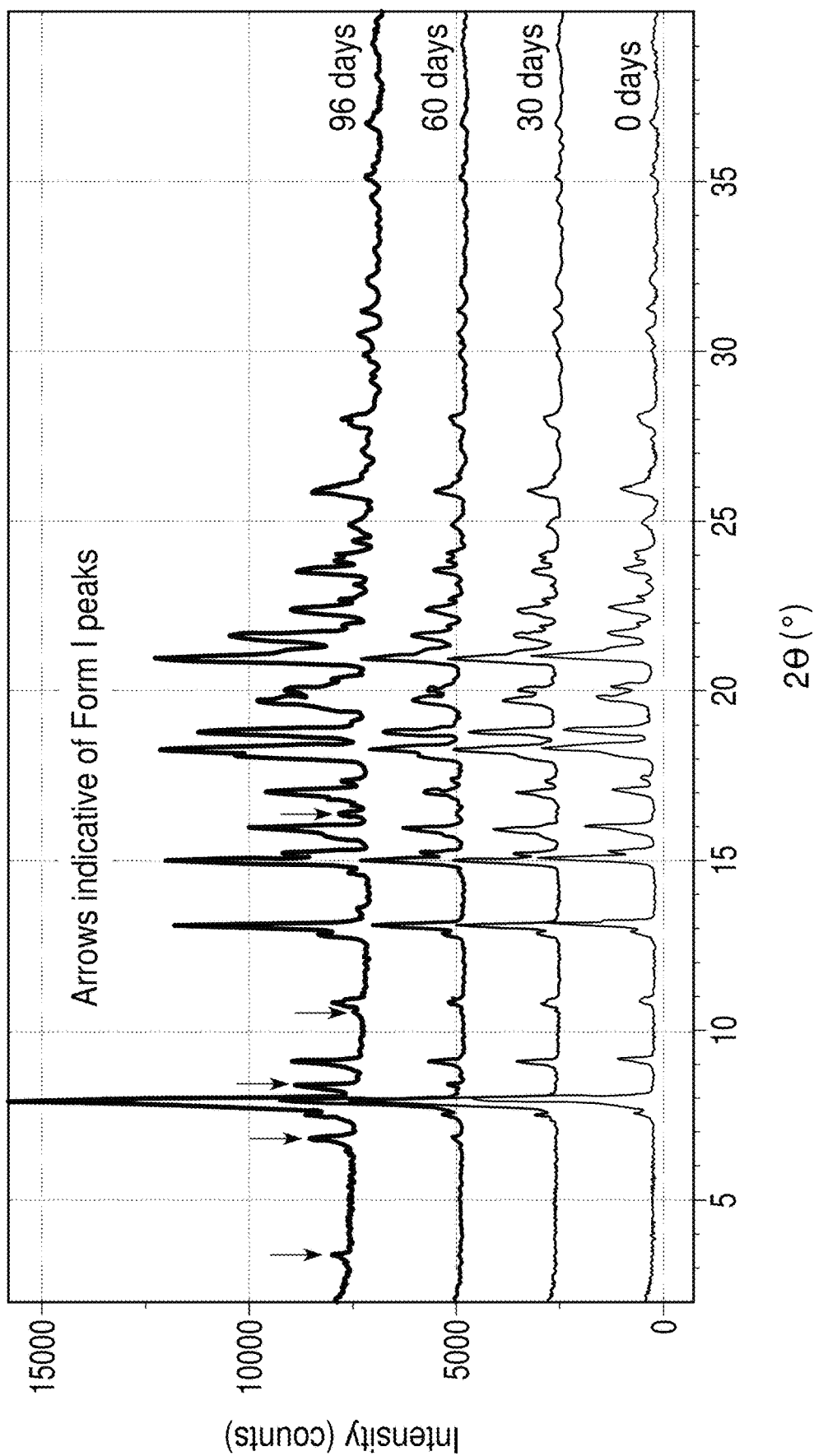

FIG. 15 provides XRPD patterns of ritonavir Form III at 40° C./75% relative humidity (RH) for 30 days, 60 days, and 96 days; arrows at 96 days indicate presence of Form I peaks in sample.

Figure 16:
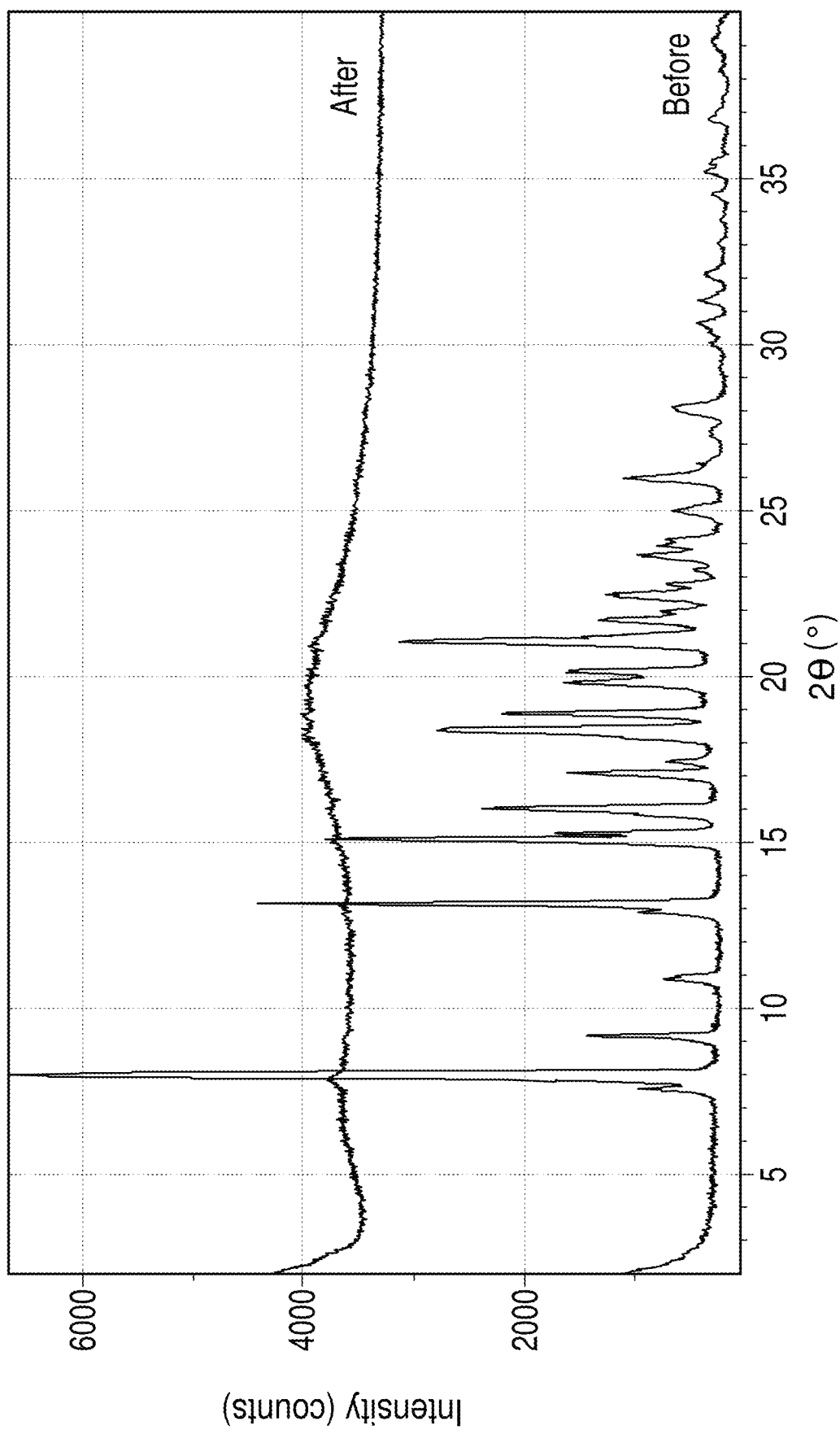

FIG. 16 provides XRPD patterns of ritonavir Form III before and after grinding.

Figure 17:
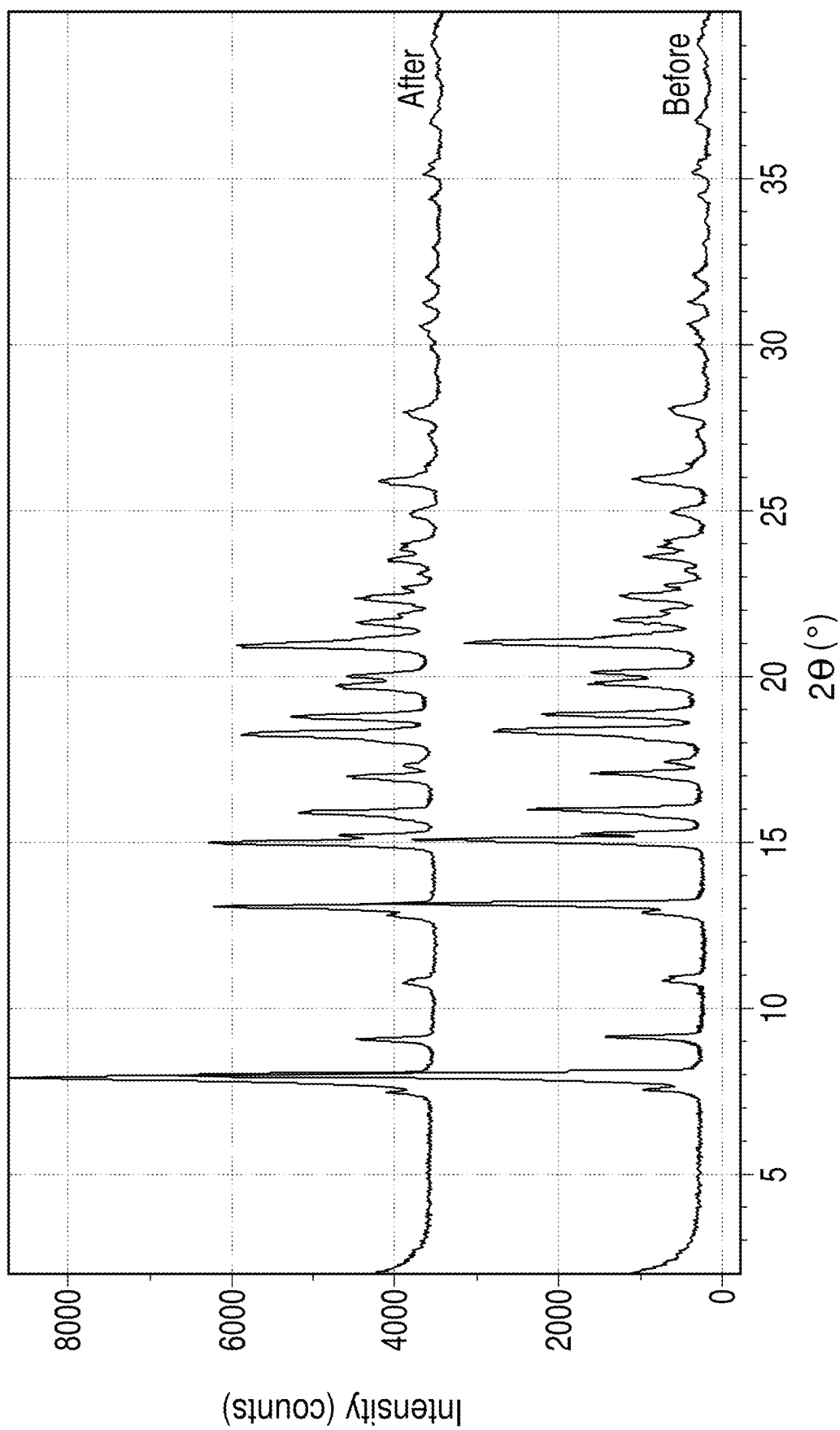

FIG. 17 provides XRPD patterns of ritonavir Form III before and after physical compression.

Figure 18:
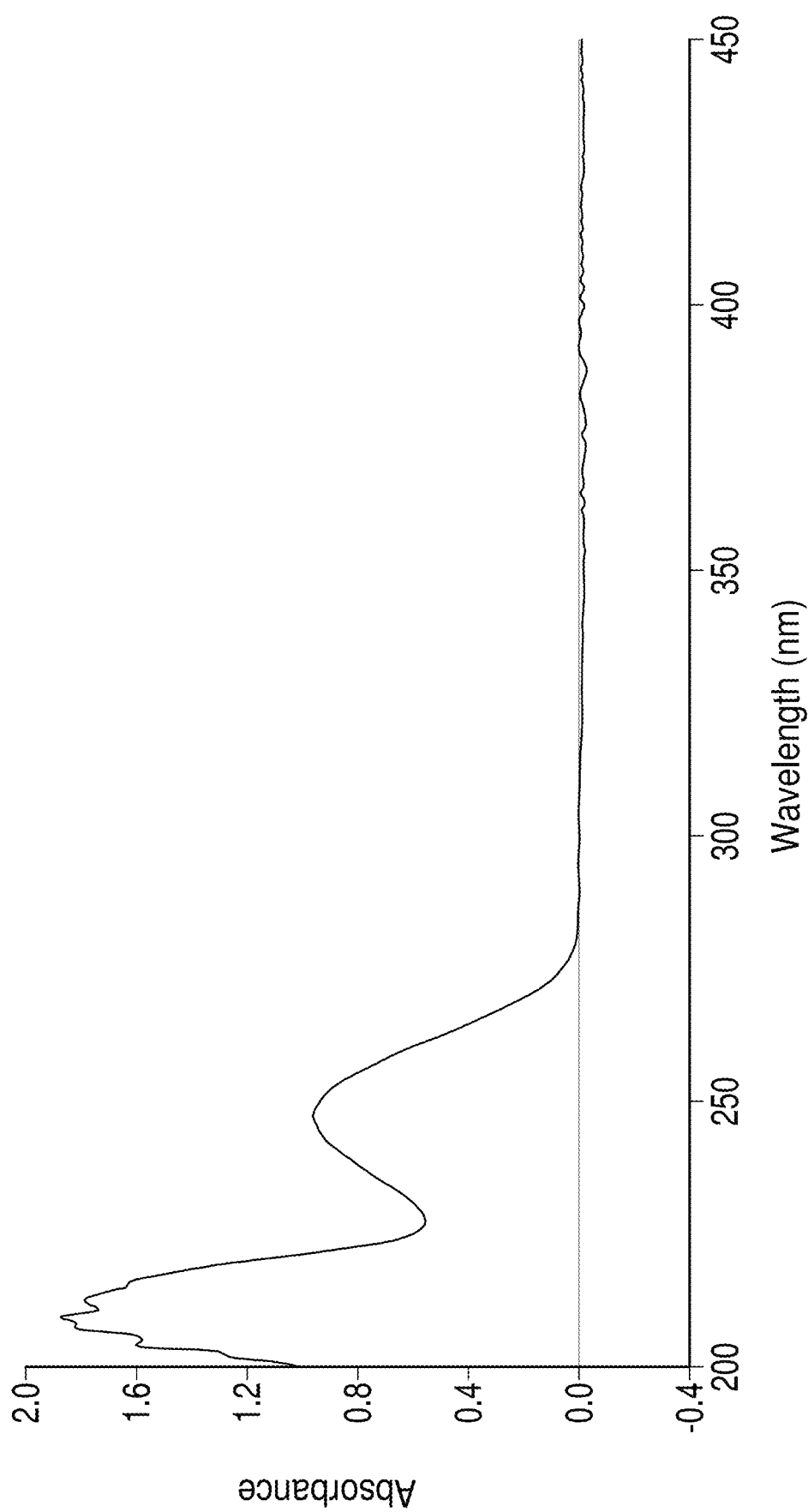

FIG. 18 provides a representative UV/VIS spectrum of ritonavir Form III solubility in 0.1N HCl after 24 hours.

Figure 19:
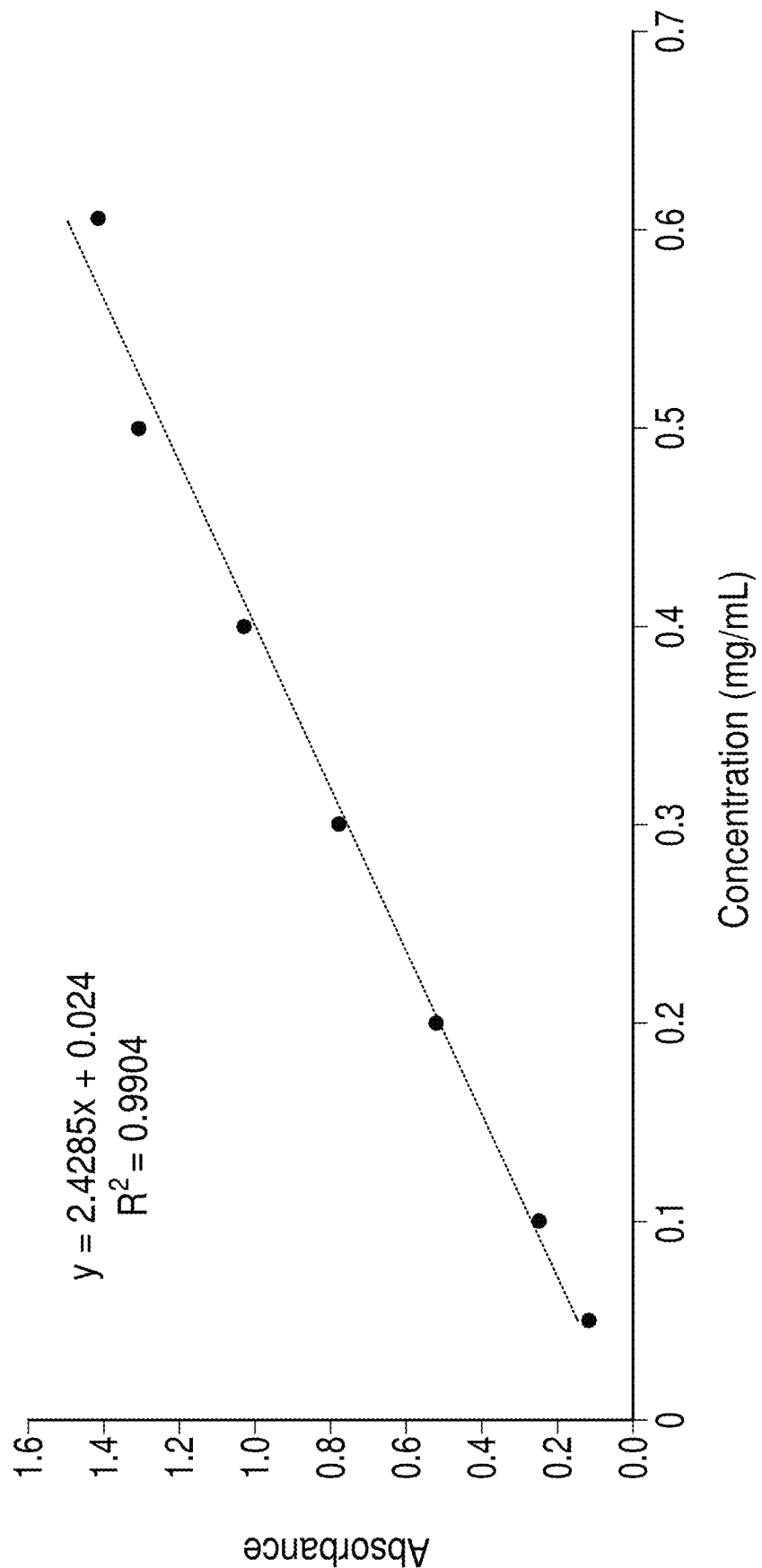

FIG. 19 provides ritonavir Form II solubility standard curve in 0.1 N HCl at 247 nm.

Figure 20:
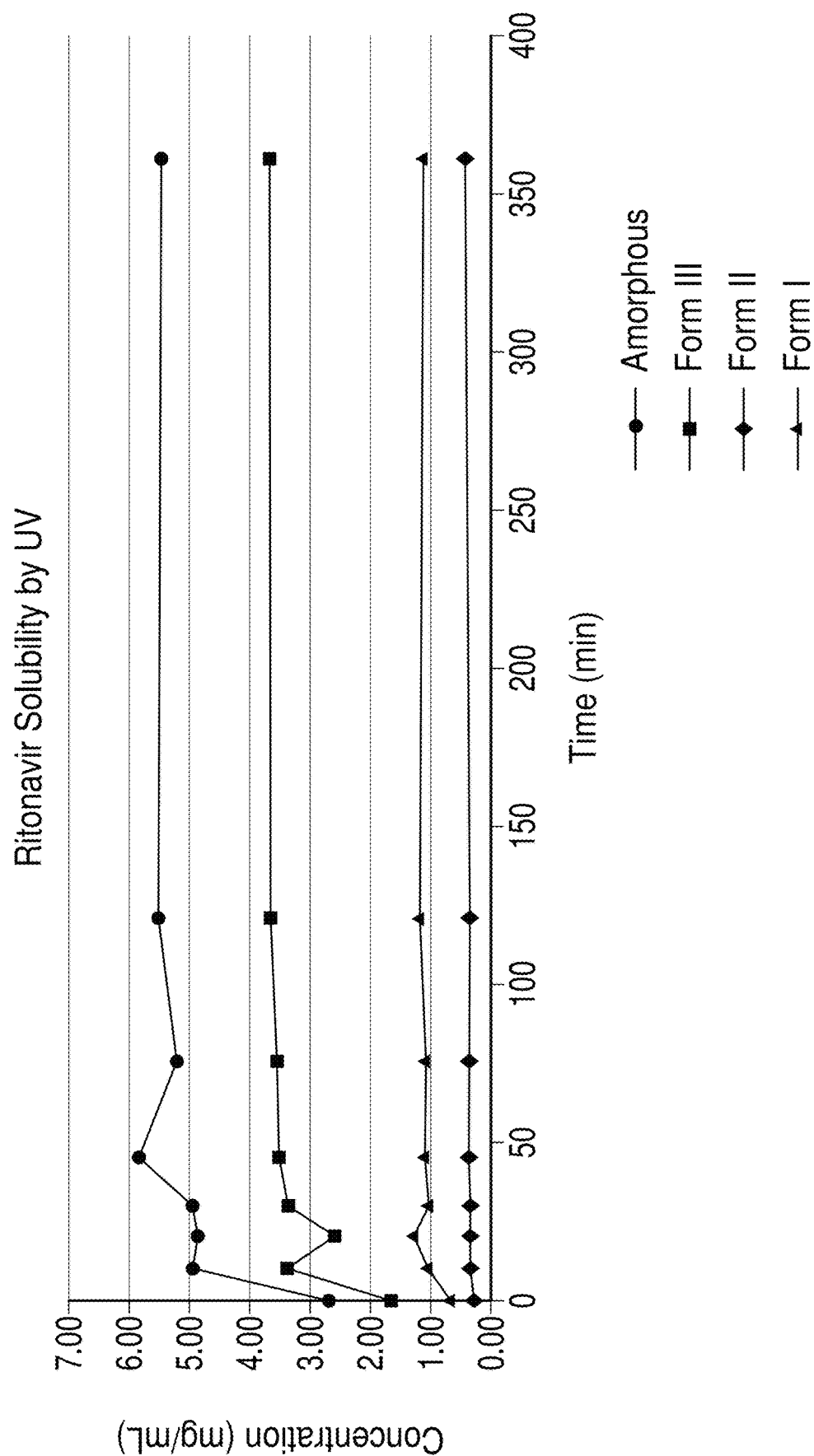

FIG. 20 provides the solubility profile of ritonavir Forms I, II, III and amorphous material in 0.1 N HCl.

Figure 21:
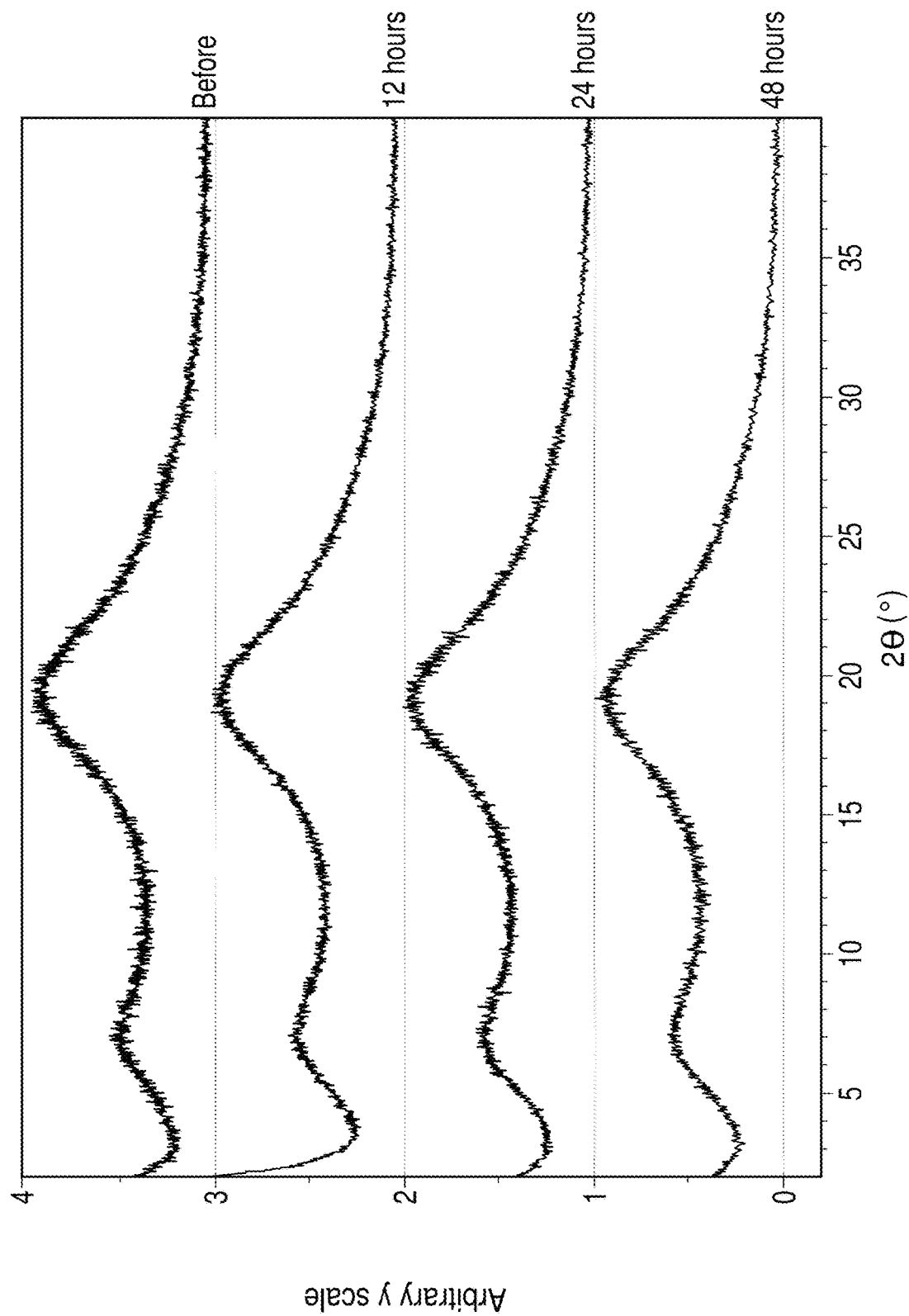

FIG. 21 provides XRPD patterns of samples collected before and after 12 h, 24 h, and 48 h during the solubility study of amorphous ritonavir in 0.1 N HCl.

Figure 22:
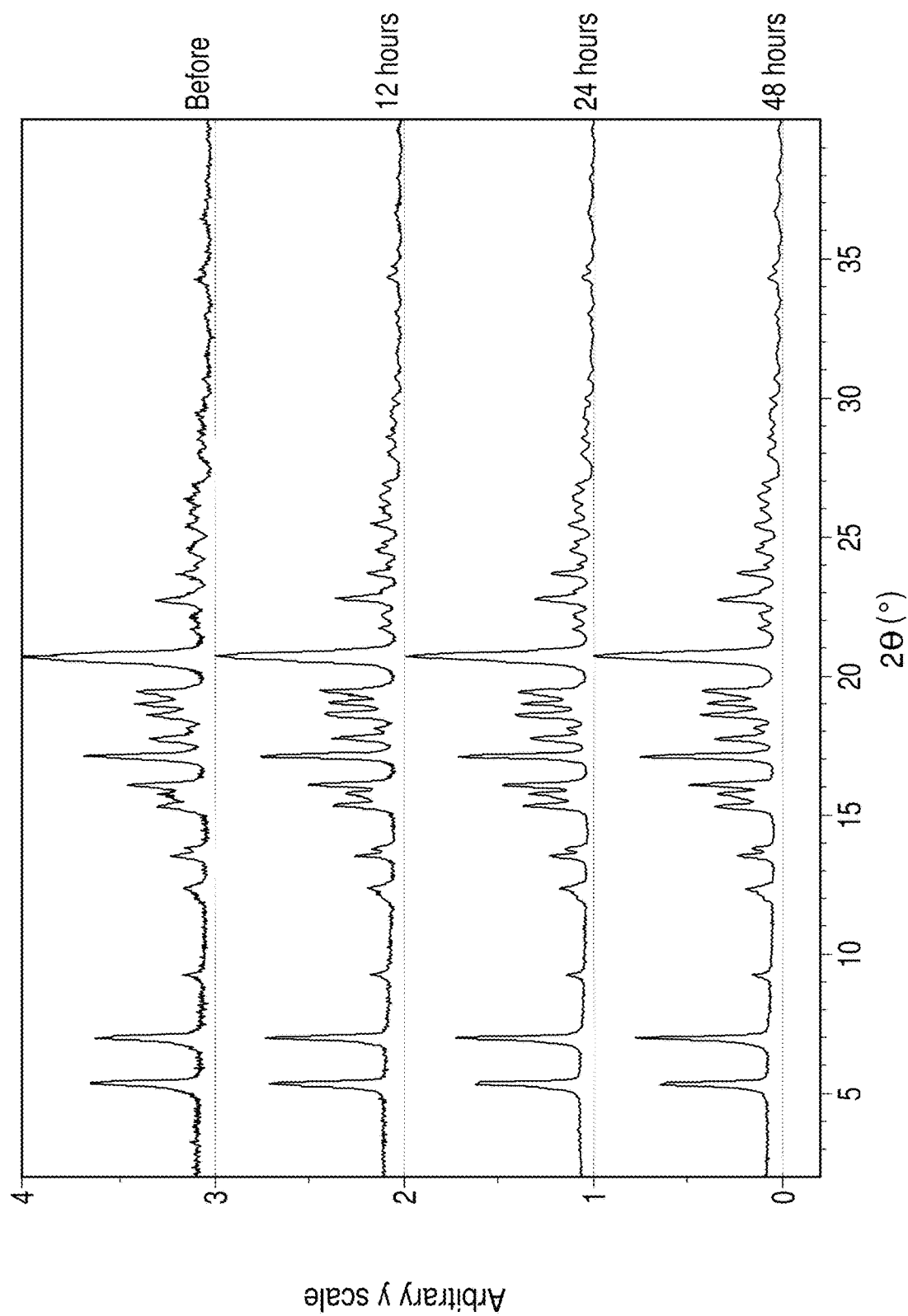

FIG. 22 provides XRPD patterns of samples collected before and after 12 h, 24 h, and 48 h during the solubility study of ritonavir Form I in 0.1 N HCl.

Figure 23:
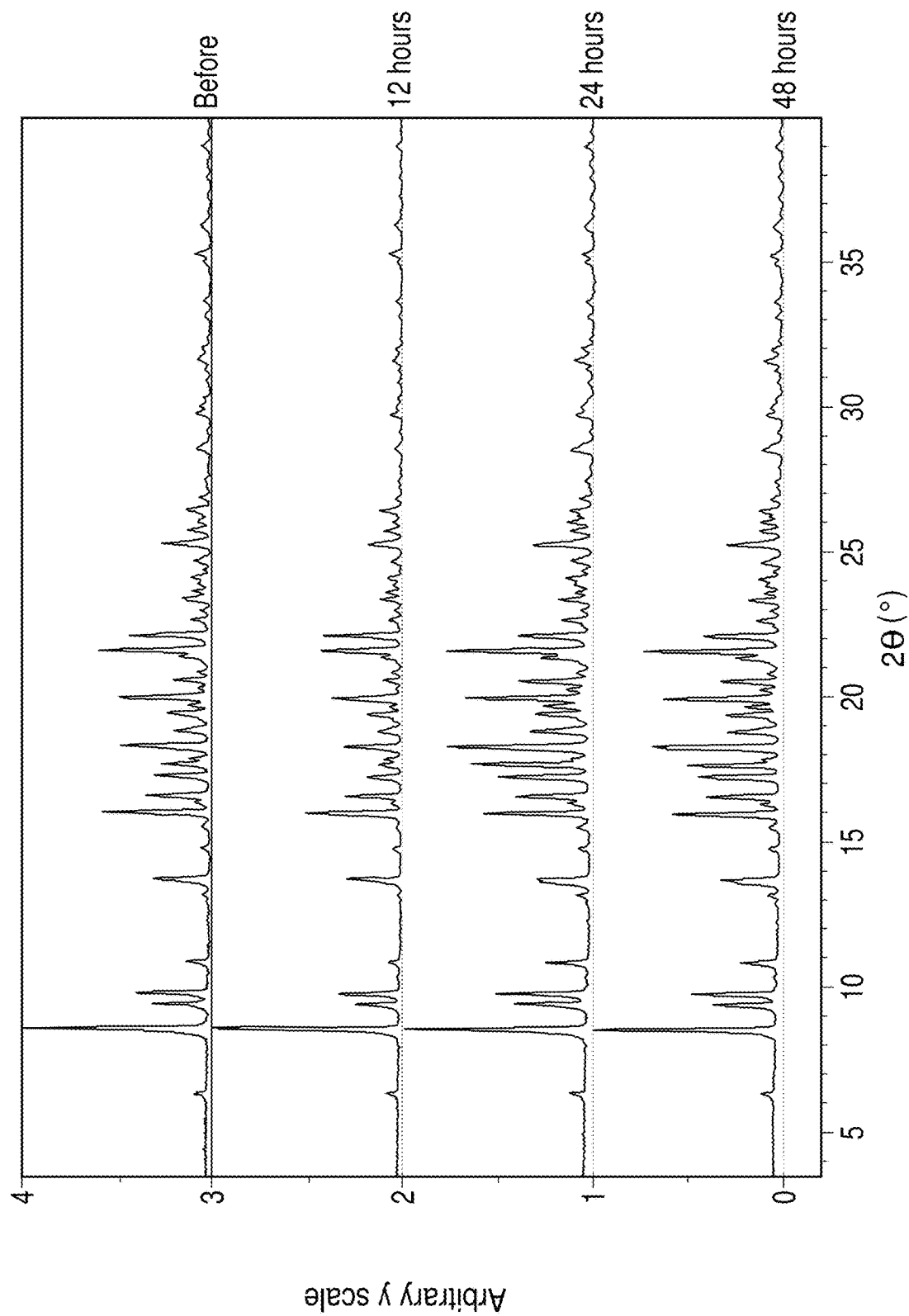

FIG. 23 provides XRPD patterns of samples collected before and after 12 h, 24 h, and 48 h during the solubility study of ritonavir Form II in 0.1 N HCl.

Figure 24:
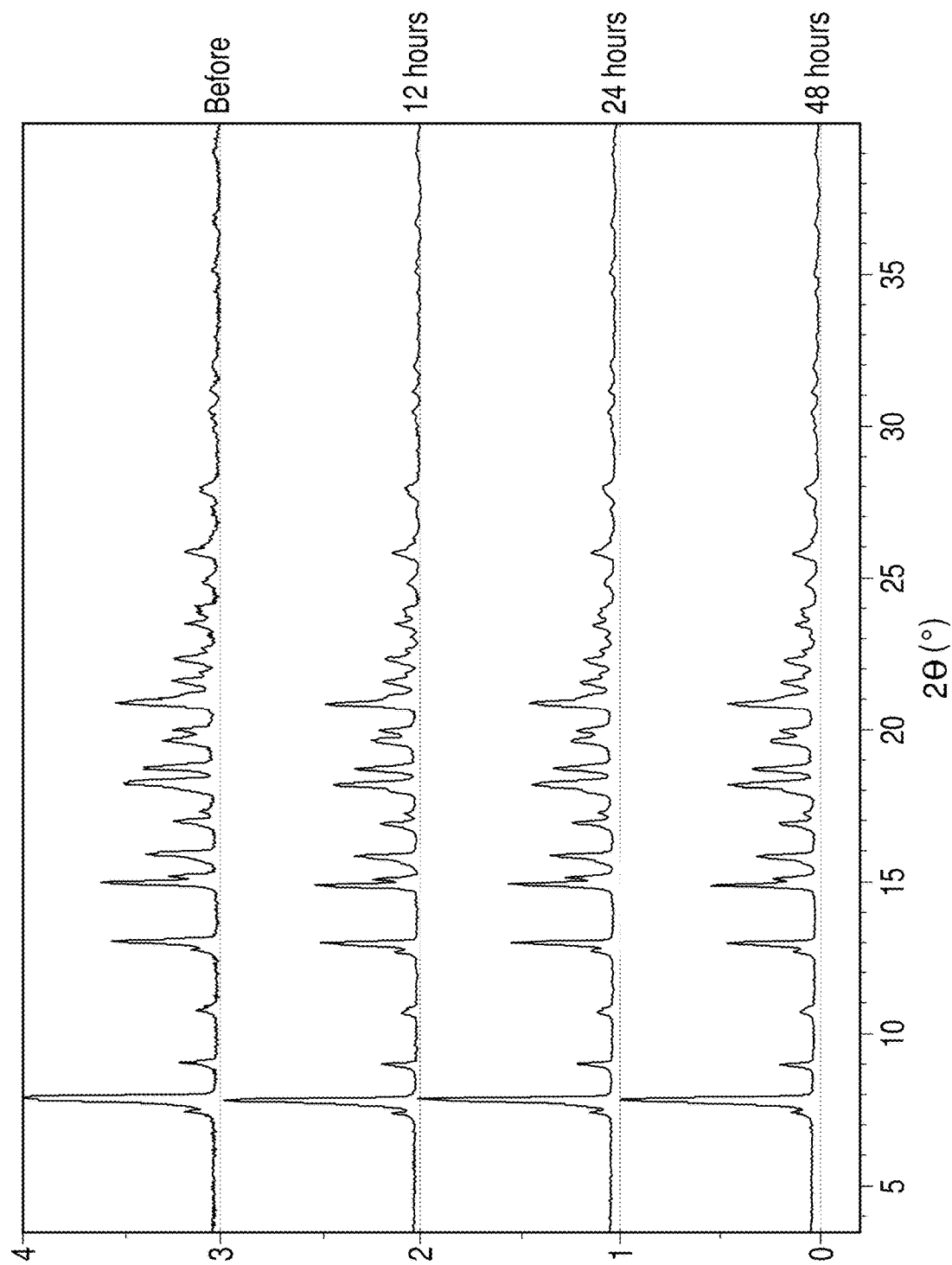

FIG. 24 provides XRPD patterns of samples collected before and after 12 h, 24 h, and 48 h during the solubility study of ritonavir Form III in 0.1 N HCl.

4. DETAILED DESCRIPTION

Many compounds can exist in different crystal forms, or polymorphs. Individual polymorphs can exhibit different physical, chemical, and spectroscopic properties. For example, certain polymorphs may be more readily soluble in particular solvents, may flow more readily, or may compress more easily than others. See, e.g., P. Damarion, et al, *J. Thermal Anal.*, 48-447-458 (1997). In the case of drugs, certain forms may be more bioavailable than others, while others may be more stable under certain manufacturing, storage, and biological conditions. This is particularly important from a regulatory standpoint, since drugs are approved by agencies such as the United States Food and Drug Administration ("FDA") only if they meet exacting purity and characterization standards. Indeed, the regulatory approval of one polymorph of a compound, which exhibits certain solubility and physico-chemical (including spectroscopic) properties, typically does not imply the ready approval of other polymorphs of that same compound.

Ritonavir is chemically named 10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester, [SS-(5R*,8R*,10R*,1R*)], and has the following structural formula.

der diffraction ("XRPD"), single-crystal X-ray diffraction, Raman spectroscopy, infrared spectroscopy, and solid-state NMR spectroscopy, among other techniques.

Different solid forms of the same compound typically exhibit distinct thermal characteristics such as melting temperature (melting point). Thermal characteristics are analyzed by such techniques as hot stage optical microscopy (HSOM), thermogravimetric analysis (TGA), and differential scanning calorimetry (DSC) to name a few. These techniques are used to identify, characterize and distinguish between various solid forms.

The data from a technique may be used in multiple ways to characterize a solid form, e.g., to confirm the presence of a particular polymorphic form. For example, the entire XRPD pattern output from a diffractometer may be used to characterize a solid form such as, for example, a polymorph of an anhydrate. A compound is polymorphic if there are two or more crystalline structures of that compound with each crystalline structure being a polymorph of the compound. A smaller subset of such data, however, may also be, and typically is, suitable for such characterization. For example, a collection of one or more peaks from such a pattern may be so used to distinguish between polymorphic forms. Indeed, often even a single XRPD peak may be used for such characterization. When a solid form herein, or a mixture of solid forms herein, is characterized by "one or more peaks" of an XRPD pattern and such peaks are listed, what is meant is that any combination of the peaks listed may be used to characterize the solid form. Further, the fact that other peaks are present in the XRPD pattern, does not negate or otherwise limit the identification of a particular polymorphic form.

An XRPD pattern is an x-y graph with °2θ (diffraction angle) (this angle is dependent on radiation wavelength which is based on a Cu source in the disclosure, for example, d-spacings were calculated using a wavelength of 1.5405929Å, the Cu-K$_{α1}$ wavelength (*Phys. Rev.* A56(6) 4554-4568 (1997)), on the x-axis and intensity on the y-axis. The pattern contains peaks which are used to characterize solid forms. The peaks are usually represented and referred to by their position on the x-axis rather than the intensity of peaks on the y-axis because peak intensity can vary due to instrumental and experimental parameters such as preferred orientation of the crystals. (see Pharmaceutical Analysis, *Lee & Web*, pp. 255-257 (2003)). Thus, intensity is not typically used by those skilled in the pharmaceutical arts to characterize solid forms.

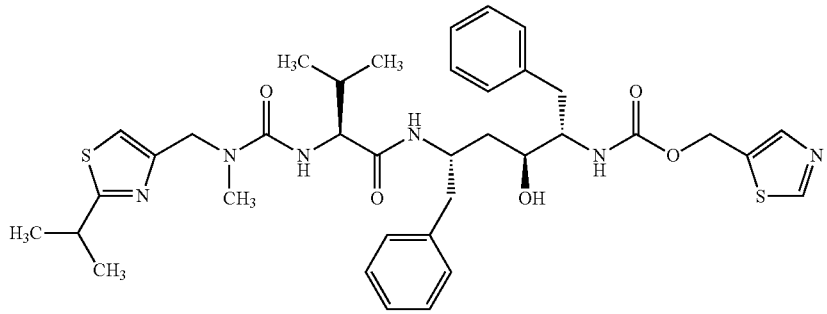 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

Various spectroscopic and crystallographic techniques are used to characterize solid forms of compounds such as anhydrates, hydrates, or solvates. These include X-ray pow- Similarly, subsets of spectra of other techniques may be used alone or in combination with other analytical data for characterization purposes. In certain embodiments, DSC measurements are used for such characterization purposes.

As with any data measurement, there is variability in X-ray powder diffraction. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts X-rays. Another source of variability comes from instrument parameters. Different X-ray instruments operate using different parameters and these may lead to slightly different diffraction patterns from the same crystalline material. Likewise, different software packages process X-ray data differently and this also leads to variability. These and other sources of variability are known to those of ordinary skill in the pharmaceutical arts.

Due to such sources of variability, it is common to recite X-ray diffraction peaks using the word "about" prior to the peak value in °2θ which presents the data to within 0.1° or 0.2° 2θ of the stated peak value depending on the circumstances. All X-ray powder diffraction peaks cited herein are reported with a variability on the order of 0.2° 2θ and are intended to be reported with such a variability whenever disclosed herein whether the word "about" is present or not.

Variability also exists in thermal measurements, such as DSC, and may also be indicative of sample purity. In certain embodiments, melting point, DSC, and hot stage microscopy data, alone or in combination with techniques such as X-ray powder diffraction, Raman spectroscopy, infrared spectroscopy or some combination thereof, are used to characterize solid forms. With respect to DSC, typical measurement variability is on the order of 1° C.

When characterizing or identifying solid forms, additional methods may be helpful when analyzing solvates or hydrates since such solid forms are different chemical entities than the corresponding anhydrates. Techniques such as solution NMR, thermal gravimetric analysis, and elemental analysis are useful in characterizing such solid forms.

There are four reported polymorphs (same chemical composition) of ritonavir that we are aware of. Forms I and II are as described in US'359 (incorporated herein by reference). Form III is as described in Yao 2022 (incorporated herein by reference) (see, FIG. 1, top XRPD pattern). And "Form IV" of ritonavir is published in Morissette et al. PNAS 2003 (incorporated herein by reference) (see FIG. 4A), which is later referred to as "Form V" ritonavir in US'413 (incorporated herein by reference) (see, FIG. 16). For clarity, this form will be referred to as "Form IV ritonavir" herein. The presently obtained crystalline form corresponds to Form III ritonavir described in Yao 2022 as confirmed, e.g., by comparison of the X-ray diffraction patterns as presented in FIGS. 1-3 discussed below.

Various other solvated forms (i.e., not polymorphs of ritonavir as they differ in chemical composition) have also been reported, including a formamide solvate termed "Ritonavir (III)", and the partially desolvated formamide solvate "Ritonavir (IV)" as described in US'413 and will not be addressed herein.

FIG. 1 shows the X-ray diffraction pattern of Form III ritonavir of the disclosure. FIG. 2 shows a comparison of Form IV ritonavir (top diffraction pattern), the Kawakami material (middle XRPD pattern) (a and b XRPD patterns), and Form III ritonavir of the disclosure (bottom XRPD pattern). The XRPD patterns are presented with the ° 2θ x-axes on the same scale, to facilitate comparison. Dotted lines extending from the diffraction pattern of Form III ritonavir of the disclosure facilitate the comparison of peaks for the several diffraction patterns of FIG. 2. As is evident, there is significant overlap in the peak positions between Form III ritonavir and the XRPD patterns (a) and (b) from Kawakami. By comparison, there is poor peak correspondence between Form IV ritonavir (Morissette el al.) and either of Kawakami's two XRPD patterns and the diffraction pattern of Form III ritonavir of the disclosure. Accordingly, it is understood that Kawakami did not reproduce Morissette el al.'s Form IV but instead produced what is now known as Form III.

FIG. 3 shows an overlay between an XRPD pattern of Form III ritonavir as prepared herein (top) and that of the newly reported Form III ritonavir from AbbVie (Yao 2022). Dotted lines illustrate very good alignment between these patterns which confirms that the AbbVie Form III ritonavir and Form III ritonavir of the present disclosure are the same polymorphic form.

Table 1 below shows observed peaks found in the X-ray powder diffraction pattern of Form III ritonavir corresponding to the XRPD pattern shown in FIG. 1.

TABLE 1

Observed XRPD Peaks for Form III ritonavir of example 1f.

| °2θ | | Intensity (%) |
|---|---|---|
| 7.46 | ±0.20 | 13 |
| 7.90 | ±0.20 | 100 |
| 9.07 | ±0.20 | 20 |
| 10.76 | ±0.20 | 9 |
| 10.87 | ±0.20 | 7 |
| 12.80 | ±0.20 | 13 |
| 13.06 | ±0.20 | 61 |
| 14.96 | ±0.20 | 52 |
| 15.17 | ±0.20 | 24 |
| 15.91 | ±0.20 | 32 |
| 16.98 | ±0.20 | 21 |
| 17.33 | ±0.20 | 9 |
| 18.23 | ±0.20 | 50 |
| 18.77 | ±0.20 | 41 |
| 19.70 | ±0.20 | 28 |
| 20.02 | ±0.20 | 20 |
| 20.94 | ±0.20 | 54 |
| 21.59 | ±0.20 | 23 |
| 21.86 | ±0.20 | 9 |
| 22.37 | ±0.20 | 21 |
| 22.66 | ±0.20 | 9 |
| 23.12 | ±0.20 | 5 |
| 23.50 | ±0.20 | 14 |
| 23.84 | ±0.20 | 10 |
| 23.98 | ±0.20 | 10 |
| 24.84 | ±0.20 | 8 |
| 25.82 | ±0.20 | 16 |
| 26.31 | ±0.20 | 4 |
| 27.28 | ±0.20 | 4 |
| 27.97 | ±0.20 | 8 |
| 29.06 | ±0.20 | 2 |
| 29.90 | ±0.20 | 3 |

Form III ritonavir may be readily distinguished from both Form I and Form II of ritonavir. The peaks in US '359 are reported to a variability of +0.1° 2θ. In Form I ritonavir, for example, a peak at 8.33° is reported. This means, that the peak could appear at °2θ values between 8.23° and 8.43°. By comparison, the closest peak in Form III ritonavir of the disclosure is about 7.90, with a variability of ±0.2° 2θ meaning the peak could appear between 7.8° and 8.1°. Accordingly, a peak at 7.9° differentiates Form III ritonavir from Form I ritonavir. The closest peak to about 7.9° in Form II ritonavir is at 8.6θ, which is even further removed than the Form I peak. Therefore, the peak at about 7.9° in Form III ritonavir also differentiates Form III ritonavir from Form II ritonavir.

Because there is one other known polymorph of ritonavir, in addition to Forms I, II and III, discussed above and referred to as Form IV ritonavir (described by Morissette et al.) herein, the choice of peaks should also be considered when compared to this polymorph. FIG. 4A of Morissette 2003 (which corresponds to the FIG. 16A of US'413) shows the XRPD pattern and peak table corresponding to Form IV ritonavir. This XRPD pattern lists 6 peaks below about 12.0° i.e.: 3.37°, 6.39°, 6.79°, 7.609°, 9.912°, and 11.25°. The variability of the peaks is not specified in either Morissette 2003 or US'413, however, variability of ±0.2°2θ is typical and will be assumed here. Using a variability of ±0.2°2θ, the peak at about 7.9° in Form III ritonavir would overlap with the peak at 7.609° in Form IV ritonavir. However, there would be no overlap between the Form III ritonavir peak at about 9.1° and the closest of Form IV ritonavir peak at 9.912°. Thus, the peak at about 9.1θ differentiates Form III ritonavir from Form IV ritonavir. Together the Form III ritonavir peaks at about 7.9° and about 9.1θ serve to differentiate from the other polymorphs of ritonavir (Form I ritonavir, Form II ritonavir, and Form IV) and therefore are appropriate to characterize Form III ritonavir.

In certain embodiments, Form III ritonavir is characterized by an X-ray powder diffraction pattern comprising peaks at about 7.9° and about 9.1θ and optionally one or more peaks selected from about 7.5°, 10.8°, about 13.1°, about 15.0θ, about 15.9θ, about 17.0θ, about 18.2°, about 18.8°, and about 20.1°. In certain embodiments, Form III ritonavir is characterized by an X-ray powder diffraction pattern comprising peaks at about 7.9° and about 9.1° and two or more peaks selected from about 7.5°, 10.8°, about 13.1°, about 15.0°, about 15.9°, about 17.0°, about 18.2°, about 18.8°, and about 20.1°. In certain embodiments, Form III ritonavir is characterized by an X-ray powder diffraction pattern comprising peaks at about 7.9° and about 9.1° and three or more peaks selected from about 7.5°, 10.8°, about 13.1°, about 15.0°, about 15.9°, about 17.0°, about 18.2°, about 18.8°, and about 20.1°. Use of the term "about" with respect to the peaks in the diffraction patterns presented herein includes ±0.2° as described above. By way of example, a peak at about 7.9° embraces peaks from 8.1° to 7.7°. Use of the term "about" in other contexts herein includes a range of ±2% of the stated value.

Form III ritonavir was indexed with a solution shown in FIG. 4. The solution included a Pawley refinement. Indexing of an XRPD pattern is a computational method that searches a set of crystallographic space group and unit cell parameters to match the observed Bragg angles in a powder pattern. If successful and all observed Bragg peaks can be attributed to the indexing solution, it is highly likely the XRPD pattern represents a single crystalline phase.

The X-ray powder diffraction pattern of Form III ritonavir prepared herein gave a suitable indexing solution as shown in FIG. 4 and the cell parameters shown below in Table 2. The calculated unit cell parameters based on the experimental diffraction pattern of Form III ritonavir are the same, within experimental error to those as characterizing the Form III published by Yao 2022.

TABLE 2

Pawley Refinement Parameters

| Space group | C2 | Cell Volume ($Å^3$) | 4031.5 |
|---|---|---|---|
| a (Å) | 23.656 | α (°) | 90 |
| b (Å) | 5.031 | β (°) | 90.572 |
| c (Å) | 33.878 | γ (°) | 90 |
| $d_{samp}$ (mm) | −0.154 | | |
| $R_{wp}$ | 6.2% | Density (g/cc) | 1.1878 |

(A broad intensity feature centered at ~20° accounts for amorphous scattering)

Stoichiometry Cell Content
Predicted unit cell volume:

$$2 \times 935.18 = 1870.36 \, Å^3.$$

Residual volume:

$$dV = 2015.8 - 1870.36 = 145.44 \, Å^3 (72.72 \, Å^3 \text{ per } asym. \text{ Unit}).$$

Form III ritonavir was also characterized herein by three thermal techniques: DSC, HSOM, and TGA. The DSC curve is displayed in FIG. 5. The sample has an endothermic onset temperature of about 114° C. indicative of the start of a melt and a peak at about 118° C. Results from the HSOM for Form III ritonavir also indicated an onset of melt temperature of about 114° C. Images of the melt onset and completion are shown in FIGS. 6A-6D, providing images captured at 115.8° C., 117.0° C., and 117.9° C. The sample was completely melted by about 118° C., and did not recrystallize upon cooling to 26.2° C.

In certain embodiments, Form III ritonavir is characterized by an endotherm onset at about 114° C., such as from 113.5° C. to 114.5° C. Such characterization may optionally be done in connection with other characteristic analytical measurements such as X-ray powder diffraction and/or Raman spectroscopy.

TG (thermogravimetric) analysis of Form III ritonavir provided herein did not indicate any appreciable weight loss (FIG. 7). DVS (dynamic vapor sorption) analysis of the presently provided Form III ritonavir shown in FIG. 8 confirmed that Form III ritonavir was not hygroscopic (very minimal weight gain), which reversed upon the desorption process. No hysteresis was observed.

Several crystals that were created during the HSOM (hot stage optical microscopy) experiments (micro crystallizations) were subsequently analyzed by Raman microscopy. At least five spectra were collected for each sample. In some cases, more than one form was found in each sample. Table 3 below summarizes the Raman findings.

TABLE 3

Raman microscopy results on HSOM experiments.

| Sample number | Raman results (spectrum number) |
|---|---|
| 50-12-01 | Amorphous (3, 5), Form III (6, 7, 10), mixture Amorphous and Form III (4, 8, 9) |
| 50-16-01 | Form II (1, 2, 3, 9), Form III (4, 5, 6, 8, 10), Unknown (7) |
| 50-24-01 | Form III (all) |
| 50-26-01 | Amorphous (1, 2, 9), Form III (8), mixture Amorphous and Form III (3, 4, 5, 6, 7, 10) |

TABLE 3-continued

Raman microscopy results on HSOM experiments.

| Sample number | Raman results (spectrum number) |
|---|---|
| 50-28-01 | Amorphous (2), Form III (1, 3, 7, 8, 10), mixture Amorphous and Form III (4, 5, 6, 9) |

Raman spectra were also obtained from example 1f. FIG. 9A and FIG. 9B display the Form III ritonavir spectrum from the macro experiment along with a representative Form III spectrum from the micro crystallization experiments (example 1c). Each spectrum is an average of 10 separate spectra collected of each sample. The Form III ritonavir spectra match.

Some stability analyses were conducted on Form III ritonavir. Short-term thermal stability experiments were conducted by holding the material from example 1f sequentially for 15 minutes at 50° C., 15 minutes at 70° C., and 15 minutes at 90° C. The sample was analyzed by Raman microscopy after each temperature exposure. In all cases, the material remained as Form III ritonavir. FIG. 10 compares the short-term thermal stability results to the reference spectra from FIG. 9.

Additionally, a longer-term stability study was performed. The Form III ritonavir from example 1c was re-analyzed after storage at ambient conditions from 5 weeks and up to 23 weeks. The Raman results are presented in FIG. 11, and the Form III ritonavir sample remained unchanged.

Under stress conditions (40° C./75% RH), conversion of Form III ritonavir to Form I ritonavir was detected at 60 days (FIG. 15). In comparison, amorphous ritonavir converted to Form I within 30 days (Table 4).

TABLE 4

Ritonavir solid forms stress test

| | 40° C./75% RH | | |
|---|---|---|---|
| Ritonavir Form | 30 days | 60 days | 96 days |
| Amorphous | Form I | Form I | Form I |
| Form I | Form I | Form I | Form I |
| Form III | Form III | Form III + Form I | Form III + Form I |

Stability Studies.

A sample of ritonavir Form III was ground manually using a mortar and pestle for five cycles of 2 minutes each (10 minutes total). XRPD analysis of the finished material showed it to be amorphous with traces of Form III (FIG. 16). Amorphous material remained unchanged after grinding. Mixture of amorphous and Form I was obtained when Form I was used and mixture of amorphous and Form II was obtained when Form II was used.

A sample of ritonavir Form III was submitted to compression at 700 lbs. XRPD analysis showed no change before and after compression (FIG. 17). Similar results were obtained when amorphous or Form I material was used.

Solubility Studies.

The solubility of ritonavir Forms I, II, III and amorphous material was measured in 0.1N HCl using UV/VIS spectroscopy. A representative UV/VIS spectrum for Form III solubility in 0.1 N HCl is shown in FIG. 18 displaying a maximum absorbance at 247 nm. The standard curve for Form II (FIG. 19) resulted in a linear regression correlation coefficient of ≥0.99 and was used to determine the concentration of materials dissolved at each time point for each studied form.

The solubility profile of ritonavir Forms I, II, III and amorphous material is shown in FIG. 20 which shows equilibrium solubility was reached for all materials evaluated by the end of the experiment (at 48 hrs). Evaluation of the recovered solids by X-ray powder diffraction (XRPD) at 12, 24, and 48 hours for each material indicated that no conversion of forms occurred during the solubility experiments (FIGS. 21 to 24). Solubility results are shown in Table 5. Form III shows superior solubility compared to Forms I and II, while showing lower solubility to amorphous material in the aqueous media studied.

TABLE 5

Solubility of solid forms of Ritonavir

| Form | Absorbance after 48 h | Concentration (mg/mL) at 48 h | Form after Solubility |
|---|---|---|---|
| Form II | 0.12 | 0.38 | Form II |
| Form I | 0.30 | 1.12 | Form I |
| Form III | 1.08 | 4.34 | Form III |
| Amorphous | 1.43 | 5.77 | Amorphous |

4.1.1. Methods of Preparing Form III Ritonavir

In certain embodiments of the methods of the disclosure, Form III ritonavir is prepared by melting a sample of ritonavir, cooling the sample to a first temperature within a nucleation temperature range for a nucleation period to thereby obtain Form III ritonavir. In these embodiments, Form III ritonavir forms at any stage of the method wherein the sample is within the nucleation temperature range, including during the initial cooling step. In additional embodiments, method further comprises the steps of holding the sample at one or more additional temperatures within the nucleation temperature range. In certain embodiments, the nucleation temperature range is from about 61° C. to about 100° C.

In certain embodiments, the sample of ritonavir to be melted is not particularly limited and is selected from any known form of ritonavir. In certain embodiments, the sample of ritonavir anhydrous. In certain embodiments, the anhydrous ritonavir is selected from one or more of amorphous ritonavir, Form I ritonavir, Form II ritonavir, and Form IV ritonavir.

In certain embodiments, the melting step includes holding the sample at a melt temperature, wherein the melt temperature is at or above the melting point of the highest melting form of ritonavir that comprises the sample and below the decomposition temperature of ritonavir. In certain embodiments, the melt temperature is at least 1° C. above the melting point of the highest melting form of ritonavir that comprises the sample. In certain embodiments, the melt temperature is below about 200° C. In certain embodiments, the melt temperature is below about 150° C. In certain embodiments, the melt temperature is below about 130° C.

In certain embodiments, the highest melting form of ritonavir in the sample is Form I ritonavir, which has a melting point of 122° C. In certain of these embodiments, the melt temperature is from about 122° C.-128° C. In further embodiments, the melt temperature is selected from at least one of 122° C., 123° C., 124° C., 125° C., 126° C., 127° C., and 128° C.

In certain embodiments, the highest melting form of ritonavir in the sample is Form II ritonavir, which has a melting point of about 125° C. In certain of these embodiments, the melt temperature is above about 125° C., e.g., 125° C.-128° C. In further embodiments, the melt temperature is selected from at least one of 125° C., 126° C., 127° C., and 128° C.

In certain embodiments, the highest melting form of ritonavir in the sample is Form IV, which has a melting point of 101° C. In certain of these embodiments, the melt temperature is above about 125° C., e.g., 125° C.-128° C.

In certain embodiments, the melt temperature is held until the sample is completely melted, that is, no solid or crystalline particles such as seed crystals remain, e.g., no solid or crystalline particles of Form I ritonavir, Form II ritonavir, or Form IV ritonavir are evident. Confirmation that the sample is completely melted is achieved by techniques known in the field, including optical microscopy such as polarized optical microscopy exemplified herein.

In certain embodiments, the melting step includes holding a sample of Form II ritonavir at a melt temperature, wherein the melt temperature is above the melting point of Form II ritonavir. In certain embodiments, the melt temperature is about 125.0° C. or greater, for example, about 125.5° C. or greater, about 126.5° C. or greater, about 127.0° C. or greater, about 127.5° C. or greater, about 128.0° C. or greater, about 128.5° C. or greater, about 129.0° C. or greater, about 129.5° C. or greater, or about 130.0° C. or greater, about 130.5° C. or greater, or about 131.0° C. or greater as long as no thermal decomposition of ritonavir is observed. In certain embodiments, the melting temperature is a range defined by any two of the preceding temperatures, for example, from about 125.0° C. to about 131.0° C., or from about 128° C. to about 131° C.

In certain embodiments, the Form II ritonavir sample is from 0.1 to 10 mg. In further embodiments, the sample is from 0.3 to 0.7 mg. In further embodiments, the sample is 0.5 mg.

In certain embodiments, the Form II ritonavir sample is from 10 to 50 mg. In certain embodiments, the Form II ritonavir sample is from 50 to 100 mg. In certain embodiments, the Form II ritonavir sample is from 100 to 200 mg. In certain of these embodiments, the sample is from 120 to 170 mg, for example 150 mg.

In certain embodiments of the provided methods, the melting step includes ramping the temperature up to a melt temperature and holding the melt temperature for a period of time, e.g., sufficient to ensure the sample has melted. This period of time will depend on the form ritonavir and the size of the sample to be melted.

In certain embodiments of the provided methods, the melt temperature is held for at least 1 minute. In further embodiments, the melt temperature is held for at least 2 minutes. In certain of these embodiments, the ritonavir sample is from 0.1 to 10 mg. In further embodiments, the sample is from 0.3 to 0.7 mg. In further of these embodiments, the sample is about 0.5 mg (e.g., 0.4-0.6 mg). In certain of these embodiments, the sample is Form II ritonavir.

In certain embodiments of the provided methods, the melt temperature is held for at least 10 minutes. In further embodiments, the melt temperature is held for at least 15 minutes. In certain of these embodiments, the ritonavir sample is from is from 100 to 300 mg. In further embodiments, the sample is from 120 to 170 mg. In further of these embodiments, the sample is 150 mg (e.g., 140-160 mg). In certain of these embodiments, the sample is Form II ritonavir.

In certain embodiments, when melting, the temperature of the Form II sample may be heated to a temperature greater than 125° C. such as between 125° C. and about 128° C. In certain embodiments, melting is done to remove all evidence of Form II crystals including seeds.

In embodiments according to the presently described methods, to achieve such a melt, one may heat at such temperatures for various lengths of time including, for example, at least 2 minutes, at least 15 minutes, and/or between about 15 and 30 minutes. HSOM may be used to visually verify melting.

In certain embodiments, nucleation and growth strategies for Form III ritonavir were determined qualitatively from HSOM micro crystallization experiments. The images shown in FIG. 12 compare relative concentration of crystals within the supercooled melt when incubated for 5 hours at each of the indicated temperatures. Under these conditions, nucleation at 100° C. did not occur (not shown). The lowest concentration of crystals is evident at both 90° C. and 70° C., indicating that nucleation and/or growth are slow at either condition. The highest concentration of crystallization under these conditions is observed at 80° C.

In certain embodiments of the provided methods, the method comprises melting the sample followed by cooling the sample to a first temperature within a nucleation temperature range, holding the sample at one or more temperatures within the nucleation temperature range for a sufficient time to obtain Form III ritonavir. In certain embodiments, the method further comprises ramping the sample temperature to one or more subsequent temperatures within the nucleation temperature range without particular limitation. In general, a subsequent temperature (i.e., a second a third a fourth and so on) may be greater or less than a prior temperature, provided that all temperatures are within the nucleation temperature range. For example, in some embodiments, the method comprises ramping the sample from the first temperature to a second temperature within the nucleation temperature range. In certain embodiments, the second temperature is greater than the first temperature. In some embodiments, the second temperature is less than the first temperature.

In certain embodiments, the nucleation temperature range is a temperature range within which crystallization of the melted sample is observed within about 5 hours, for example, about 3 hours, about 2 hours, about 1 hour, about 50 minutes, about 40 minutes, about 30 minutes, about 25 minutes, about 20 minutes, about 15 minutes, about 8 minutes, or about 5 minutes.

In certain embodiments, the nucleation temperature is a temperature range within which crystallization of the melted sample is completed within about 40 hours, about 37 hours, about 35 hours, about 30 hours, about 25 hours, about 23 hours, about 20 hours, about 15 hours, about 10 hours, about 9 hours, about 8 hours, about 7 hours, about 6 hours, about 5 hours, about 4 hours, about 3 hours, about 2 hours, or about 1 hour.

In embodiments of the method provided herein, the nucleation temperature range is from about 60° C. to about 100° C. In certain embodiments, the nucleation temperature range is selected from about 61° C. to about 100° C. In certain embodiments, the nucleation temperature range is from about 70° C. to a temperature selected from 80° C., 81° C., 82° C., 83° C., 84° C., 85° C. In certain embodiments, the nucleation temperature range is from about 70° C. to about 85° C. In certain embodiments, the nucleation temperature range is from 60° C. to 100° C. In certain embodiments, the nucleation temperature range is from 65° C. to 100° C. In certain embodiments, the nucleation temperature range is from 70° C. to 100° C. In certain embodiments, the nucleation temperature range is from 75° C. to 100° C. In certain embodiments, the nucleation temperature range is from 80° C. to 100° C. In certain embodiments, the nucleation temperature range is from 85° C. to 100° C. In certain embodiments, the nucleation temperature range is from 90° C. to 100° C. In certain embodiments, the nucleation temperature range is from 60° C. to 95° C. In certain embodiments, the nucleation temperature range is from 60° C. to 90° C. In certain embodiments, the nucleation temperature range is from 60° C. to 85° C. In certain embodiments, the nucleation temperature range is from 60° C. to 80° C. In certain embodiments, the nucleation temperature range is from 60° C. to 75° C. In certain embodiments, the nucleation temperature range is from 60° C. to 70° C. In certain embodiments, the nucleation temperature range is from 60° C. to 65° C. In certain embodiments, the nucleation temperature range is from 65° C. to 95° C. In certain embodiments, the nucleation temperature range is from 70° C. to 90° C. In certain embodiments, the nucleation temperature range is from 75° C. to 85° C. In certain embodiments, the nucleation temperature is 76 77, 78, 79, 80, 81, 82, 83, 84, or 85° C. In certain embodiments, the nucleation temperature is 76° C. In certain embodiments, the nucleation temperature is 77° C. In certain embodiments, the nucleation temperature is 78° C. In certain embodiments, the nucleation temperature is 79° C. In certain embodiments, the nucleation temperature is 80° C. In certain embodiments, the nucleation temperature is 81° C. In certain embodiments, the nucleation temperature is 82° C. In certain embodiments, the nucleation temperature is 83° C. In certain embodiments, the nucleation temperature is 84° C. In certain embodiments, the nucleation temperature is 85° C.

In certain embodiments, the first or subsequent temperature within the nucleation temperature range is selected from 61° C., 62° C., 63° C., 64° C., 65° C., 66° C., 67° C., 68° C., 69° C., and 70° C. 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., and 100° C. In certain embodiments, the first or subsequent temperature within the nucleation temperature range is selected from 80° C., 81° C., 82° C., 83° C., 84° C., 85° C., 86° C., 87° C., 88° C., 89° C., and 90° C. In certain embodiments, the first or subsequent temperature within the nucleation temperature range is selected from 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., and 90° C. In certain embodiments, the first or subsequent temperature within the nucleation temperature range is selected from 70° C., 71° C., 72° C., 73° C., 74° C., 75° C., 76° C., 77° C., 78° C., 79° C., 80° C., 81° C., 82° C., 83° C., 84° C., and 85° C.

In certain embodiments, the sample is held within a nucleation temperature range until the sample crystallizes. In certain embodiments, the time the sample is held within a nucleation temperature range is the nucleation period. In certain embodiments, the nucleation period is about 40 hours, up to about 37 hours, up to about 35 hours, up to about 30 hours, up to about 25 hours, up to about 23 hours, about 20 hours, up to about 15 hours, up to about 10 hours, up to about 9 hours, up to about 8 hours, up to about 7 hours, up to about 6 hours, up to about 5 hours, up to about 4 hours, up to about 3 hours, up to about 2 hours, or up to about 1 hours. In additional embodiments, the nucleation temperature range is between about 70° C. and 85° C. or between about 70° C. and about 80° C. In particular embodiments, the nucleation period is between 1 hour and 48 hours, including up to about 37 hours, up to about 23 hours, or less. In some embodiments, the sample melted is from 0.5 mg to 300 mg, but much larger samples may be used.

In certain embodiments, after the nucleation period, the sample is then held at a recovery temperature. In certain embodiments, the recovery temperature is below the glass transition temperature of amorphous ritonavir. In certain embodiments, the recovery temperature is below 42° C.

In certain embodiments, the transition between temperatures e.g., ambient to melt temperature, melt to a first temperature, first temperature to second temperature, or any temperature within the nucleation temperature range to the recovery temperature, is not particularly limited and includes a temperature ramp rate of 20°/min, 15°/min, 10°/min, 8°/min, 6°/min, 4°/min and 2°/min.

In certain embodiments, the methods of the disclosure are performed under standard gravity conditions on Earth. In alternative embodiments, the methods of the disclosure are performed or under reduced gravity conditions found, for example, in earth orbit in a satellite.

FIG. 13 compares the crystal concentration after 5 and 8 hours within the same supercooled melt when held at the ideal temperature, providing a visual representation of the relative crystallization rate achieved. Additional HSOM micro crystallization experiments also determined that (1) first nucleating Form III at a cooler temperature before incubating at a slightly higher temperature did not increase the overall rate of crystallization, while (2) the quench rate from the melt to the incubation temperature does influence the nucleation rate.

By applying a general rule of thumb, guidelines based on previously studied systems and the measured glass transition temperature of amorphous ritonavir, Yao, 2022 assumes the maximum nucleation rate from the melt can only be achieved within a narrow temperature range of 60-70° C. As such, Yao, 2022 first nucleated Form III ritonavir at 60° C. for two days, and then continued its growth at 90° C. for an additional two days. However, based on the empirical methodology developed herein, it was determined that these two temperatures are suboptimal for both nucleation and continued growth of Form III ritonavir from the supercooled melt. Rather, 80° C. was identified as a superior nucleation and hold temperature. Using the conditions illustrated in FIG. 14, Form III ritonavir was nucleated from the melt within less than 20 minutes, and in at least one example, nucleation occurred at 7 minutes and 35 seconds at a micro scale and to nucleate and crystallize completely within 23 hours at a macro scale.

The present disclosure further provides for Form III ritonavir made by the methods herein and pharmaceutical compositions of Form III ritonavir, whether made in accordance with the disclosure or otherwise, further comprising one or more pharmaceutically acceptable excipients. The disclosure further provides methods of treating HIV, COVID-19, or any condition treated by inhibiting cytochrome P450-3A4 comprising administering to a patient in need thereof a therapeutically effective amount of Form III ritonavir such as a pharmaceutical composition thereof.

4.1.2. Pharmaceutical Compositions and Dosage Forms

Pharmaceutical compositions and dosage forms of the present disclosure comprise Form III ritonavir prepared by the presently disclosed methods, typically in combination with one or more pharmaceutically acceptable excipients, and optionally in combination with one or more additional pharmacologically active compounds. Examples of additional pharmacologically active compounds include, but are not limited to, PIs, NRTIs, and NNRTIs, such as those disclosed herein. Other additional pharmacologically active compounds include, but are not limited to, immunosuppressants, chemotherapeutic agents, antifungals, and antibiotics.

Single unit dosage forms of the present disclosure, in certain embodiments, are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as hard gelatin, HPMC, starch, and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the present disclosure will typically vary depending on their use. For example, a dosage form suitable for mucosal administration may contain a smaller amount of active ingredient(s) than an oral dosage form used to treat the same indication. This aspect of the present disclosure will be readily apparent to those skilled in the art. See, e.g., REMINGTON'S PHARMACEUTICAL SCIENCES, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition. Consequently, the present disclosure encompasses pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient.

Lactose-free compositions of the present disclosure can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

The present disclosure further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-380. Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the present disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

The present disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the present disclosure comprise Ritonavir in an amount of from about 50 mg to about 1000 mg, preferably in an amount of from about 75 mg to about 750 mg, and most preferably in an amount of from about 100 mg to about 500 mg.

Enumerated Embodiments

1. A method for obtaining Form III ritonavir; wherein the method comprises the steps of: melting a sample of ritonavir;
   cooling the sample to a first temperature within a nucleation temperature range for a nucleation period; and
   obtaining Form III ritonavir.
2. The method according to embodiment 1, wherein the method further comprises:
   holding the temperature at the first temperature for a nucleation period; and optionally ramping the sample from the first temperature to a second temperature;
   wherein the first and second temperatures are within the nucleation temperature range.
3. The method according to embodiment 1 or 2, wherein the nucleation temperature range is from above 60° C. to about 100° C., such as from 70° C. to 90° C. or 75° C. to 85° C., including wherein the nucleation temperature range is about 80° C.

4. The method according to any one of embodiments 1-3, wherein the X-ray powder diffraction pattern of Form III ritonavir comprises peaks at about 7.9° and about 9.1° 2θ.
5. The method according to embodiment 4, wherein the X-ray powder diffraction pattern of Form III ritonavir further comprises:
   (a) one or more peaks at about 7.5°, 10.8°, about 13.1°, about 15.0°, about 15.9°, about 17.0°, about 18.2°, about 18.8°, and about 20.1° 2θ;
   (b) peaks at about 7.90°, 13.06°, 14.96°, 18.23°, 18.77°, and 20.94° 2θ; or
   (c) peaks at about 7.90°, 13.06°, 14.96°, 15.17°, 15.91°, 18.23°, 18.77°, 19.70°, and 20.94° 2θ.
6. The method according to any one of embodiments 1-5, wherein the differential scanning calorimetry thermogram of Form III ritonavir has an endotherm with an onset temperature of about 114° C.
7. The method according to any one of embodiments 1-6, wherein the form of the ritonavir sample to be melted is selected from amorphous ritonavir, Form I ritonavir, Form II ritonavir, or Form IV ritonavir.
8. The method according to any one of embodiments 1-7, wherein the form of the ritonavir sample to be melted is Form II ritonavir.
9. The method according to any one of embodiments 1-8, wherein the melting step comprises ramping the temperature of the sample to a melt temperature of 125° C. or greater.
10. The method according to embodiment 9, wherein the melt temperature is between about 125° C. to about 128° C.
11. The method according to embodiment 9 or 10, wherein the melt temperature is above the melting point of Form II ritonavir and held until the entire sample is melted.
12. The method according to embodiment 9 or 10, wherein the melt temperature is above the melting point of Form II ritonavir and held until no crystalline particles are visible.
13. The method according to any one of embodiments 9 to 12, wherein the melt temperature is above the melting point of Form II ritonavir and held until no seed crystals of Form II are present in the melt.
14. The method according to any one of embodiments 9 to 13, wherein the melt temperature is held for at least two minutes.
15. The method according to embodiment 14, wherein the melt temperature is held for at least 15 minutes.
16. The method according to embodiment 15, wherein the melt temperature is held between about 15 minutes and about 30 minutes.
17. The method according to any preceding embodiment, wherein the nucleation temperature range is from about 70° C. to about 85° C.
18. The method according to embodiment 17, wherein the first nucleation temperature is about 80° C.
19. The method according to any preceding embodiment, wherein the nucleation period is between 1 hour and 48 hours, such as between 1 hour and 23 hours.
20. The method according to embodiment 19, wherein the nucleation period is about 23 hours.
21. The method according to embodiment 19, wherein the nucleation period is about 37 hours.
22. The method according to any preceding embodiment, wherein the obtained Form III ritonavir comprises a mixture of amorphous ritonavir and Form III ritonavir.
23. The method according to any preceding embodiment, wherein crystallization of the sample is substantially complete during the nucleation period.
24. The method according to any preceding embodiment, further comprising the step of cooling the obtained Form III ritonavir.
25. The method according to embodiment 24, wherein the obtained Form III ritonavir is cooled to a temperature below the glass transition temperature of amorphous ritonavir.
26. The method according to any preceding embodiment, wherein the obtained Form III ritonavir forms within the nucleation temperature range.
27. The method according to any preceding embodiment, wherein the amount of ritonavir in the sample to be melted is between about 0.5 mg and about 5000 mg, such as between about 0.5 mg and about 2000 mg, between about 0.5 mg and about 1000 mg, between about 0.5 mg and about 700 mg, and between about 0.5 mg and about 300 mg.
28. The method according to any preceding embodiment, wherein the melting step is complete upon absence of any crystalline material as observed by HSOM.
29. The method according to any preceding embodiment, wherein the nucleation period is performed under reduced gravity conditions.
30. The method according to embodiment 29, wherein the reduced gravity conditions occur in a spacecraft in orbit around the Earth.
31. A Form III ritonavir prepared by the methods of any one of embodiments 1 to 30.
32. The pharmaceutical composition comprising Form III ritonavir according to embodiment 31, and one or more pharmaceutically acceptable excipients.
33. The pharmaceutical composition comprising Form III ritonavir according to embodiment 31, one or more additional pharmaceutically active ingredients, and one or more pharmaceutically acceptable excipients.
34. The pharmaceutical composition according to embodiment 33, wherein the one or more additional pharmaceutically active ingredients comprises nirmatrelvir or a pharmaceutically acceptable salt thereof.
35. The pharmaceutical composition according to embodiment 33, wherein the one or more additional pharmaceutically active ingredients comprises lopinavir or a pharmaceutically acceptable salt thereof.
36. A method of treating one or more of HIV or COVID-19 comprising administering to a patient need thereof a pharmaceutically acceptable amount of Form II ritonavir according to embodiment 31 or a pharmaceutical composition according to any one of embodiments 33-35.
37. A method of inhibiting cytochrome P450-3A4 comprising administering to a patient need thereof a pharmaceutically acceptable amount of Form III ritonavir according to embodiment 31 or a pharmaceutical composition according to any one of embodiments 33-35.

5. EXAMPLES

5.1. Example 1. Methods for Obtaining Polymorphic "Form III" of Ritonavir 5.1.1. Crystallization (Micro)

Form III was first confirmed via Raman microscopy of several samples created during various hot stage optical microscopy (HSOM) experiments. For each experiment, a small portion (~0.5 mg) of Ritonavir Form II was placed on a scrupulously clean microscope slide. The sample was not covered with a cover glass. The Linkam LTS420 hot stage with T95 temperature controller was programmed with various temperature ramp routines, as described below in Table 6.

TABLE 6

Thermal Profiles of Ritonavir Micro-Crystallization

|  | Sample 1a | Sample 1b | Sample 1c | Sample 1d | Sample 1e |
|---|---|---|---|---|---|
| Step 1 | Heat 40° C./min to 127.0° C. hold for 1 min | Heat 40° C./min to 127.0° C. hold for 1 min | Heat 40° C./min to 127.0° C. hold for 1 min | Heat 40° C./min to 127.0° C. hold for 1 min | Heat 40° C./min to 127.0° C. hold for 2 min |
| Step 2 | Cool 20° C./min to 70° C. hold for 20 hrs | Cool 20° C./min to 80° C. hold for 20 hrs | Cool 20° C./min to 80° C. hold for 20 hrs | Cool 20° C./min to 30° C. hold for 8 hrs | Cool 20° C./min to 30° C. hold for 1 hr |
| Step 3 | Cool 2° C./min to 30° C. hold for 5 hr | Cool 2° C./min to 30° C. hold for 4 hrs | Cool 2° C./min to 30° C. hold for 5 hrs | Cool 2° C./min to 30° C. hold for 5 hrs | Heat 2° C./min to 80° C. hold for 10 hrs |
| Step 4 | N/A | N/A | N/A | N/A | Cool 2° C./min to 30° C. hold for 10 hrs |

Directly upon completion of the hot stage temperature ramp routine, a few crystals of the sample were transferred to either a gold-coated microscope slide or a fused-silica microscope slide and analyzed by Raman microscopy.

5.1.2. Crystallization (Macro)

Example 1f. A 150.0 mg sample of Ritonavir USP lot M-RIT/0804007 Form II was flattened on a glass slide to provide a solid compact of uniform thickness of approximately 1 mm×17 mm×17 mm (289 mm$^3$) in size. Using a drying oven, the compact was melted by exposure to 125 to 128° C. for 17 minutes. Temperatures near the vicinity of the sample were measured with a mercury thermometer. The complete melt was confirmed visually. The sample was held at 128° C. for an additional 10 minutes to ensure that no crystalline particles of Form II remained within the melt. The melt was immediately transferred to a second drying oven and placed near a mercury thermometer, also within the oven, measuring 80° C. and retained there for 37 hours. The sample, undisturbed from the glass slide, was removed from the oven and observed with an Olympus SZX9 stereomicroscope under crossed polarizers as a dense mat of birefringent needles. The material was removed from the glass slide and rendered into a powder and analyzed by X-ray powder diffraction, Raman microspectroscopy, and differential scanning calorimetry. The assigned sample number for this material was 48-69-07.

Example 1g. A 150.0 mg sample of Ritonavir USP lot M-RIT/0804007 Form II was flattened on a glass slide to provide a solid compact of uniform thickness of approximately 1 mm×17 mm×17 mm (289 mm3) in size. Using a drying oven, the compact was melted by exposure to 125 to 128° C. for 27 minutes. Temperatures near the vicinity of the sample were measured with a mercury thermometer. The melt was immediately transferred to a second drying oven and placed near a mercury thermometer, also within the oven, measuring 80° C. and retained there for 23 hours. The sample, undisturbed from the glass slide, was removed from the oven and observed with an Olympus SZX9 stereomicroscope under crossed polarizers as a dense mat of birefringent needles. The material was removed from the glass slide and rendered into a powder and analyzed by X-ray powder diffraction as Form III. The assigned sample number for this material was 48-89-01.

Example 1h. A 651.4 mg sample of Ritonavir USP lot M-RIT/0804007 Form II was flattened on a glass slide to provide a solid compact of uniform thickness of approximately 1 mm×17 mm×17 mm (289 mm$^3$) in size. Using a drying oven, the compact was melted by exposure to about 130° C. for about 25 minutes. Temperatures near the vicinity of the sample were measured with a mercury thermometer. The complete melt was confirmed visually. The melt was immediately transferred to a second drying oven and placed near a mercury thermometer, also within the oven, measuring 80° C. and retained there for about 24 hours. The sample, undisturbed from the glass slide, was removed from the oven, allowed to cool to room temperature, and observed under a microscope where some crystals were seen. The sample was returned to the second drying oven at 80° C. and retained there overnight. No change was observed under the microscope. The sample was then transferred to a third drying oven and placed near a mercury thermometer, also within the oven, measuring 130° C. for about 1 minute to melt. The temperature in the oven was reduced slowly to about 83° C. and the sample retained there overnight. A solid white/tan mass was observed. The sample was removed from the oven and allowed to cool to room temperature. The material appeared crystalline under the microscope. The material was removed from the glass slide and rendered into a powder and analyzed by X-ray powder diffraction, Raman microspectroscopy, and differential scanning calorimetry. The assigned sample number for this material was 01-89-01.

5.2. Example 2. Characterization of Form III 5.2.1. X-ray Powder Diffraction

The XRPD pattern was collected on the material crystallized from the macro crystallization with a PANalytical Empyrean diffractometer in Bragg-Brentano geometry using a Cu radiation source (Cu K-alpha 1) generated at 45 kV/40 mA. A silicon standard was analyzed to check the instrument alignment. Prior to the analysis, a specimen of the sample was packed into a silicon zero background diffraction holder with a 10×0.2 mm well and analyzed in reflection geometry. The X-ray source was configured with Soller slits of 0.04 radians, a fixed anti-scatter slit of ¼°, a mask of 4 mm, and a fixed divergence slit of ¹⁄₁₆°. The diffracted beam passed through a 7.5 mm anti-scatter slit and large Soller slit of 0.02 radians to the detector. Diffraction patterns were collected with Data Collector software v.6.1b using a PIXcel3D-Medipix3 1×1 detector located 240 mm from the specimen. The data was acquired using 12 repetitions of a continuous scan from 2 to 40° 2θ with sample spinning at a revolution time of 2 seconds.

5.2.2. Indexing and Pawley Refinement

Topas 6 (TOPAS 6.0.0.9, 2018, Bruker AXS GmbH, Karlshruhe, Germany) was used for Indexing and Pawley refinements. Refinements were performed on all parameters simultaneously to a convergence of 0.001 in $\chi^2$. Refined unit cell parameters, space group and fit residual as well as a graphical representation of the Pawley refinement result were determined. Further refinement parameters included but may not be limited to the following: The background was modeled using a Chebychev polynomial function and a 1/x contribution to account for air scattering. If needed, further broad scattering features may be modeled by a broad first principle peak contribution.

Bragg peaks were fitted to a first principles peak function with Gaussian crystallite size broadening ($\tau_G$), and Lorentzian strain broadening ($\varepsilon_L$). Peak asymmetry due to axial divergence was modeled using the simple axial model (SAM) with a start value of 10 mm. Sample displacement ($d_{samp}$)/Zero error ($z_0$) correction was used to account for Bragg peak shifts and listed in the parameter table if used.

5.2.3. Differential Scanning Calorimetry

DSC was performed using a TA Instruments model Q10 differential scanning calorimeter. The instrument was calibrated using indium. The sample was placed into a standard aluminum DSC pan, covered with a lid, and the weight was accurately recorded. An aluminum pan configured as the sample pan was placed on the reference side of the cell. The pan lid was crimped prior to sample analysis. Samples were analyzed in a single run from 25 to 200° C. at a heating rate of 10° C./min under nitrogen gas.

5.2.4. Hot Stage Optical Microscopy (HSOM)

Analyses were completed using an Olympus BX51TRF polarized light microscope using crossed-polarizers, a 20×, 0.40 Numerical Aperture, LM PLAN FL N objective, and a first-order red compensator (530 nm). Heating was conducted with a Linkam LTS420 hot stage with a T95 LinkPad system controller. Images were acquired with a Lumenera Series Infinity 3-3URC (Teledyne Lumenera, Ottawa, Ontario, Canada) digital camera. Image capture and image processing using Image-Pro® version 10.0.12 Build 7452 (Date: 1 Apr. 2020).

Determination of melting point was examined using sample 48-69-07, the macro crystallization experiment. A small portion of sample was placed onto a scrupulously clean microscope slide. The sample was covered with a No. 1½ cover glass. The Linkam hot stage system controller was programmed with the following temperature ramp routine:
1) Heat at 5.00° C./min to 113.7° C.
2) Heat at 2.00° C./min to 119.0° C.

Thermal stability was assessed by exposing Form III sequentially to 50° C., 70° C., and then 90° C. for 15 minutes at each temperature point, followed by Raman analysis (sample 50-54-01).

5.2.5. Thermogravimetric Analysis

TG analysis was performed on a TA Instruments Discovery TGA 55 using Platinum sample and reference pans. The temperature calibration was performed with nickel. The sample was placed into the pan, heated at 10° C./min. from ambient to a final temperature of 200° C. under a balance nitrogen purge of 40 mL/min.

5.2.6. Dynamic Vapor Sorption

DVS isotherms were characterized using a VTI SGA-100 Vapor Sorption Analyzer. The sample was not dried prior to analysis. Sorption and desorption isotherms were collected over a range from 5% to 95% RH at 10% RH increments under a dry air purge. The equilibrium criterion used for analysis was less than 0.0100%/weight change in five minutes with a maximum equilibration time of three hours and a 2-minute data logging interval. Data were not corrected for the initial moisture content of the sample.

5.2.7. Raman Microscopy

A HORIBA Scientific XploRA Series Confocal Raman Microscope (Piscataway, NJ) was used to collect Raman spectra using the following parameters: 785 nm laser at 100% power, 1200 g/mm grating, 300 micrometer confocal hole, 100 micrometer slit entrance to the spectrograph, 1 second spectral acquisition with 30 accumulations. The Raman signal is detected using a Syncrity Model 356399, thermoelectrically cooled-CCD detector. Spectra were acquired over the range-125 to 1800 $cm^{-1}$. An Olympus Series BX51TRF polarized light microscope (Olympus America Inc., Melville, NY) provided the base optical platform. An Olympus MPlan N Series 20×, 0.40 NA microscope objective was used to focus the laser light onto the sample and to collect the Raman signal. The microscope was equipped with a Marzhauser Wetzlar computer-controlled mapping stage to translate the sample for focus and data acquisition. Digital images were acquired using a Lumenera Series Infinity 3-1C (Teledyne Lumenera, Ottawa, Ontario, Canada) camera using Infinity software version 6.5.6 and Infinity Analyze software version 7.0.2.930 (Build date 1May 2020). System calibration was performed prior to each analysis using a silicon disc to monitor peak position at 520.7 $cm^{-1}$. All calibrations passed specifications prior to data collection.

The sample was prepared by placing a small amount of material from the hot stage melt recrystallization experiment onto either a gold-coated microscope slide or a fused-silica microscope slide using a tungsten needle and dispersed to a thin layer. The small sample was illuminated with white light using 200× magnification for specific sample area analysis. Analyses was conducted on what appeared microscopically to be a single crystal whenever possible.

The same instrument parameters were used for all Raman microspectroscopy data collection.

Additional Instrument Parameters

Autofocus: on
AutoExposure: off
Spike Filter: Multiple accumulations
Delay Time: zero seconds
Binning: 1
Readout Mode. Signal
DeNoise: Lite
ICS Correction: off
Dark Correction: off
Instrument Process: off
Detector Gain: Best Dynamic Range
Detector ADC: 45 kHz
Laser Polarization: Circular
Raman Polarization: None
Collection Time: 1:30 seconds

5.3. Example 3. Stability Studies

5.3.1. Temperature and Humidity Stress

A sample of ritonavir Form III was stored at 40° C. and 75% RH. XRPD was measured at 30, 60, and 96 days (FIG. 15). Presence of Form I was detected starting at 60 days. No change was observed when amorphous or Form I ritonavir material was used (Table 5).

5.3.2. Manual Grinding

A sample of ritonavir Form III was ground manually using a mortar and pestle for five cycles of 2 minutes each (10 minutes total). XRPD analysis of finished material showed it to be amorphous with traces of Form III (FIG. 16). Amorphous material remained unchanged after grinding. Mixture of amorphous and Form I was obtained when Form I was used and mixture of amorphous and Form II was obtained when Form II was used.

5.3.3. Compression

A sample of ritonavir Form III was submitted to compression at 700 lbs. XRPD analysis showed no change before and after compression. Similar results were obtained when amorphous or Form I material was used.

5.4. Example 4. Solubility Studies 5.4.1. Sample Preparation and Analysis

Approximately 24 mg of Form I and approximately 60 mg of Forms I, II, and amorphous material were weighed into eleven separate 20-mL scintillation vials each containing 2 mL of 0.1 N HCl solution and magnetic stir bar. Each vial was tightly capped and placed into a heating/chilling dry block (Torrey Pines) on an orbital shaker (Four E's) adjusted to 210 rpm. The vials were allowed to shake for up to 48 hours at ambient conditions. At the following times (0, 10, 20, 30, 45, 60, 75, 120, 360, 720, 1440, and 2880 minutes), the contents of one vial/form were subsequently centrifuged at 5000 rpm for 5 minutes to obtain clear supernatants. If needed, the supernatant was transferred to a clean tube and re-centrifuged for an additional 5 minutes. Each supernatant was diluted 10-fold with 0.1 N HCl solution and analyzed by UV/VIS at 0, 10, 20, 30, 45, 75 min, 2 h, 6 h, 12 h, 24 h, and 48 h.

5.4.2. Standard Preparation

A 6 mg/mL stock solution was made by accurately weighing ~30 mg of Ritonavir Form II into a 5 mL volumetric flask, adding 3 mL methanol to dissolve the solids, and then diluting to volume with methanol. Standard solutions ranging from 0.5 mg/mL to 5 mg/mL were made by diluting the stock solution in methanol followed by further dilution of each of the solutions in 0.1 N HCL to achieve calibration standards ranging from 0.05 mg/mL to 0.6 mg/mL.

5.4.3. UV-VIS Analysis

All analyses were conducted on a Photonics CCD Array UV/VIS Spectrophotometer equipped with a deuterium lamp, a fiber optic dip probe (0.2 cm path length) using a range of 200 to 450 nm and Spectral Instruments SI 400 Series Spectrophotometer Software Part #1657, Rev. C software. The dip probe was rinsed with water and methanol in between all measurements. Prior to measurements, the spectrophotometer was blanked with the 0.1 N HCl solution.

5.4.4. Solid Sample Recovery

After the 12-hour, 24-hour, and 48-hour of solubility testing of Forms I, II, III and amorphous material, the remaining solids that followed centrifugation were re-suspended with remaining supernatant, filtered using a nylon filter (Swinnex system, Omnipore 0.2 μm, nylon filter, lot #0000160371), and allowed to air-dry.

5.4.5. 5.2.1.1 X-Ray Powder Diffraction Analysis

XRPD patterns were collected as described above, except that the data were acquired using up to 6 repetitions from 2-40° 2θ with sample spinning at a revolution time of 2 seconds.

6. EQUIVALENTS AND INCORPORATION BY REFERENCE

While the claimed invention has been particularly shown and described with reference to a preferred embodiment and various alternate embodiments, it will be understood by persons skilled in the relevant art that various changes in form and details can be made therein without departing from the spirit and scope of the present disclosure.

All references, issued patents, and patent applications cited within the body of the present disclosure, are hereby incorporated by reference in their entirety, for all purposes, including but not limited to benefit of U.S. Provisional Application No. 63/510,042, filed on Jun. 23, 2023, U.S. Provisional Application No. 63/404,090, filed on Sep. 6, 2022, and U.S. Provisional Application No. 63/403,258, filed on Sep. 1, 2022, the content of each of which is hereby incorporated by reference.

What is claimed is:

1. A method for obtaining Form III ritonavir, wherein the method comprises the steps of:
    melting a sample of ritonavir;
    cooling the sample to a first temperature within a nucleation temperature range for a nucleation period, wherein the nucleation temperature range is from about 75° C. to about 100° C.;
        wherein the nucleation period is between 1 and 23 hours;
        crystallization of Form III ritonavir is substantially complete during the nucleation period; and
    obtaining Form III ritonavir.

2. The method according to claim 1, wherein the method further comprises:
    holding the temperature at the first temperature for a nucleation period; and
    ramping the sample from the first temperature to a second temperature;
    wherein the first and second temperatures are within the nucleation temperature range.

3. The method according to claim 1, wherein the X-ray powder diffraction pattern of Form III ritonavir comprises peaks at about 7.9° 2θ and about 9.1° 2θ.

4. The method according to claim 1, wherein the form of the ritonavir sample to be melted is selected from amorphous ritonavir, Form I ritonavir, and Form II ritonavir.

5. The method according to claim 4, wherein the form of the ritonavir sample to be melted is Form II ritonavir.

6. The method according to claim 1, wherein the melting step comprises ramping the temperature of the sample to a melt temperature of 125° C. or greater.

7. The method according to claim 6, wherein the melt temperature is between about 125° C. to about 128° C.

8. The method according to claim 6, wherein the form of the ritonavir sample to be melted is Form II ritonavir; and
    the melt temperature is above the melting point of Form II ritonavir and is held until no seed crystals of Form II ritonavir are present in the melt.

9. The method according to claim 6, wherein the melt temperature is held for at least two minutes.

10. The method according to claim 6, wherein the melt temperature is held for at least 15 minutes.

11. The method according to claim 6, wherein the melt temperature is held between about 15 minutes and about 30 minutes.

12. The method according to claim 1, wherein the nucleation temperature range is from about 75° C. to about 85° C.

13. The method according to claim 12, wherein the first temperature is about 80° C.

14. The method according to claim 1, wherein the obtained Form III ritonavir comprises a mixture of amorphous ritonavir and Form III ritonavir.

15. The method according to claim 1, wherein the sample or ritonavir crystallizes and the crystallization is substantially complete during the nucleation period.

16. The method according to claim 1, further comprising the step of cooling the obtained Form III ritonavir, and wherein the obtained Form III ritonavir is cooled to a temperature below the glass transition temperature of amorphous ritonavir.

17. The method according to claim 1, wherein the obtained Form III ritonavir forms within the nucleation temperature range.

18. The method according to claim 1, wherein the amount of ritonavir in the sample to be melted is between about 0.5 mg and about 5000 mg.

19. The method according to claim 1, wherein the melting step is complete upon absence of any crystalline material as observed by hot stage optical microscopy.

20. The method according to claim 1, wherein the nucleation period is performed under reduced gravity conditions.

* * * * *